(12) United States Patent
Bader et al.

(10) Patent No.: US 12,179,041 B2
(45) Date of Patent: Dec. 31, 2024

(54) APPARATUS, SYSTEM, AND METHOD FOR MECHANICAL ABLATION WITH THERAPEUTIC ULTRASOUND

(71) Applicant: THE UNIVERSITY OF CHICAGO, Chicago, IL (US)

(72) Inventors: Kenneth B. Bader, Chicago, IL (US); Viktor Bollen, Chicago, IL (US)

(73) Assignee: THE UNIVERSITY OF CHICAGO

( * ) Notice: Subject to any disclaimer, the term of this patent is extended or adjusted under 35 U.S.C. 154(b) by 495 days.

(21) Appl. No.: 16/809,732

(22) Filed: Mar. 5, 2020

(65) Prior Publication Data

US 2020/0282239 A1    Sep. 10, 2020

Related U.S. Application Data

(60) Provisional application No. 62/814,570, filed on Mar. 6, 2019.

(51) Int. Cl.
*A61N 7/00* (2006.01)
*A61B 8/08* (2006.01)
*A61B 8/14* (2006.01)

(52) U.S. Cl.
CPC .............. *A61N 7/00* (2013.01); *A61B 8/0833* (2013.01); *A61B 8/14* (2013.01);
(Continued)

(58) Field of Classification Search
CPC .............. A61N 7/00; A61N 2007/0004; A61N 2007/0039; A61N 2007/0052; A61N 7/02;
(Continued)

(56) References Cited

U.S. PATENT DOCUMENTS

2008/0319356 A1* 12/2008 Cain ................. A61M 37/0092
                                                              600/300
2009/0178483 A1*  7/2009 Angelsen ............ G01S 7/52022
                                                              73/597
(Continued)

FOREIGN PATENT DOCUMENTS

WO    2019081329 A1 †  5/2019

OTHER PUBLICATIONS

Apfel, Robert E., "Acoustic Cavitation" *Methods in Experimental Physics* 1981, 19, 355-411.
(Continued)

*Primary Examiner* — Hien N Nguyen
(74) *Attorney, Agent, or Firm* — Norton Rose Fulbright US LLP

(57) ABSTRACT

This disclosure describes devices, systems, and methods related to therapeutic ultrasound. An exemplary system includes a transducer configured to emit therapy ultrasound waves towards a therapy site and an ultrasound imaging device configured to emit plane wave ultrasound waves towards the therapy site. The system further includes a controller coupled to the transducer and the ultrasound imaging device. The controller is configured to send an activation signal to the transducer and send an activation signal to the ultrasound imaging device. The controller is further configured to receive image data from the ultrasound imaging device and generate bubble cloud image data based on the received image data.

20 Claims, 17 Drawing Sheets

(52) U.S. Cl.
CPC .................. *A61N 2007/0004* (2013.01); *A61N 2007/0039* (2013.01); *A61N 2007/0052* (2013.01)

(58) Field of Classification Search
CPC ......... A61B 8/0833; A61B 8/14; A61B 8/085; A61B 8/481
See application file for complete search history.

(56) References Cited

U.S. PATENT DOCUMENTS

| | | | |
|---|---|---|---|
| 2014/0135681 A1* | 5/2014 | Angelsen | A61N 7/00 604/22 |
| 2016/0242741 A1* | 8/2016 | Wan | G16H 50/30 |
| 2019/0196013 A1* | 6/2019 | Stanziola | A61B 8/06 |
| 2019/0314001 A1* | 10/2019 | Maresca | G01S 7/52085 |
| 2020/0107817 A1* | 4/2020 | Provost | A61B 8/481 |

OTHER PUBLICATIONS

Arnal et al., "In vivo real-time cavitation imaging in moving organs" *Phys. Med Biol.* 2017, 62,843-57.

Bader et al., "Efficacy of histotripsy combined with rt-PA in vitro" *Phys Med Biol.* 2016, 61(14), 5253-5274.

Bader et al., "For whom the bubble grows: Physical principles of bubble nucleation and dynamics in histotripsy ultrasound therapy" *Ultrasound Med Biol.* 2018, 45(5), 1056-1080.

Bader et al., "Observation and modulation of the dissolution of histotripsy-induced bubble clouds with high-frame rate plane wave imaging" *Phys. Med Biol.* 2019, 64, 115012-115015.

Bader et al., "Post Hoc Analysis of Passive Cavitation Imaging for Classification of Histotripsy-Induced Liquefaction in Vitro" *IEEE Trans. Med Imaging* 2018, 37, 106-15.

Bader et al., "Predicting the growth of nanoscale nuclei by histotripsy pulses" *Phys. Med Biol.* 2016, 2947-66.

Bader et al., "The effect of frequency-dependent attenuation on predicted histotripsy waveforms in tissue mimicking phantoms" *Ultrasound Med Biol.* 2016, 42(7), 1701-1705.

Bader et al., "The influence of gas diffusion on bubble persistence in shock-scattering histotripsy" *The Journal of the Acoustical Society of America* 2018, 143(6), EL481-EL486.

Bader, Kenneth B., "The influence of medium elasticity on the prediction of histotripsy-induced bubble expansion and erythrocyte viability" *Phys Med Biol.* 2018, 63(9): 095010, 35 pages.

Bader, Kenneth B., and Christy K. Holland, "Gauging the likelihood of stable cavitation from ultrasound contrast agents" *Phys. Med Biol.* 2012, 58, 127-44.

Canney et al., "Shock-induced heating and millisecond boiling in gels and tissue due to high intensity focused ultrasound" *Ultrasound in Medicine & Biology* 2010, 36(2), 250-67.

Canney et al., "Tissue Erosion Using Shock Wave Heating and Millisecond Boiling in HIFU Fields" *AIP Conference Proceedings* 2010, 1215(1).

Church et al., "A theoretical study of inertial cavitation from acoustic radiation force impulse imaging and implications for the mechanical index" *Ultrasound Med Biol.* 2015, 41(2), 472-485.

Church, C C. "A theoretical study of cavitation generated by an extracorporeal shock wave lithotripter" *J Acoust Soc Am.* 1989, 86(1), 215-27.

Church, C C. "Prediction of rectified diffusion during nonlinear bubble pulsations at biomedical frequencies" *J Acoust. Soc. Am.* 1988, 83, 2210-17.

Couture et al., "Ultrasound contrast plane wave imaging" *IEEE Trans. Ultrasan., Ferroelect., Freq. Contr.* 2012, 59(12), 2676-2683.

Crum, Lawrence A., and Gary M. Hansen. "Generalized equations for rectified diffusion" *J. Acoust. Soc. Am.* 1982, 72 1586-92.

Duryea et al., "Removal of Residual Cavitation Nuclei to Enhance Histotripsy Fractionation of Soft Tissue" *IEEE Trans Ultrason Ferroelectr Freq Control.* 2015, 62(12), 2068-2078.

Duryea et al., "Removal of Residual Cavitation Nuclei to Enhance Histotripsy Erosion of Model Urinary Stones" *IEEE Trans. Ultrasan., Ferroelect., Freq. Contr.* 2015, 62(5), 896-904.

Eller, Anthony. "Rectified Diffusion during Nonlinear Pulsations of Cavitation Bubbles" *The Journal of the Acoustical Society of America* 1965, 37(3), 493.

Gateau et al., "Combined passive detection and ultrafast active imaging of cavitation events induced by short pulses of high-intensity ultrasound" *IEEE Trans. Ultrasan., Ferroelect., Freq. Contr.* 2011, 58(3), 517-532.

Hall et al., "A real-time measure of cavitation induced tissue disruption by ultrasound imaging backscatter reduction" *IEEE Trans. Ultrasan., Ferroelect., Freq. Contr.* 2007, 54(3), 569-575.

Hall, Tim, and Charles Cain. "A Low Cost Compact 512 Channel Therapeutic Ultrasound System For Transcutaneous Ultrasound Surgery" *AIP Conference Proceedings* 2006, 829, 445.

Haworth et al., "Using Passive Cavitation Images to Classify High-Intensity Focused Ultrasound Lesions" *Ultrasound in Medicine & Biology* 2015, 41(9), 2420-2434.

Holland, C.K. and R.E. Apfel. "An improved theory for the prediction of microcavitation thresholds" *IEEE transactions on ultrasonics, ferroelectrics, and frequency control* 1989, 36, 204-208.

Hu et al., "Spatial-temporal ultrasound imaging of residual cavitation bubbles around a fluid-tissue interface in histotripsy" *The Journal of the Acoustical Society of America* 2015, 137, 2563-2572.

Khokhlova et al., "Controlled tissue emulsification produced by high intensity focused ultrasound shock waves and millisecond boiling" *J. Acoust. Soc. Am.* 2011, 130(5), 3498-3510.

Khokhlova et al., "Histotripsy methods in mechanical disintegration of tissue: Towards clinical applications" *International Journal of Hyperthermia* 2015, 31(2), 145-162.

Landu, L.D., and E.M. Lifshitz. *Fluid Mechanics* vol. 6. Pergamon Press, 1987.

Lastman, G.J. and R.A. Wentzell, "Comparison of five models of spherical bubble response in an inviscid compressible liquid" *Journal of the Acoustical Society of America* 1981, 69, 638-642.

Maxwell et al., "A Prototype Therapy System for Transcutaneous Application of Boiling Histotripsy" *IEEE Trans. Ultrasan., Ferroelect., Freq. Contr.* 2017, 64(10), 1542-1557.

Maxwell et al., "Cavitation clouds created by shock scattering from bubbles during histotripsy" *The Journal of the acoustical Society of America* 2011, 130(4), 1888-1898.

Maxwell et al., "Disintegration of tissue using high intensity focused ultrasound: Two approaches that utilize shock waves" *Acoustics Today* Aug. 2012, 24-37.

Maxwell et al., "Inception of cavitation clouds by scattered shockwaves" *IEEE International Ultrasonics Symposium* 2010, 108-111.

Maxwell et al., "Noninvasive Treatment of Deep Venous Thrombosis Using Pulsed Ultrasound Cavitation Therapy (Histotripsy) in a Porcine Model" *Journal of Vascular and Interventional Radiology* 2011, 22, 369-377.

Maxwell et al., "Probability of Cavitation for Single Ultrasound Pulses Applied to Tissues and Tissue-Mimicking Materials" *Ultrasound in Medicine & Biology* 2013, 39(3), 449-465.

Muhr, Alan H., and John M.V. Blanshard, "Diffusion in gels" *Polymer* 1982, 23(7), 1012-1026.

Neppiras, E.A., "Acoustic cavitation" *Physics Reports* 1980, 61(3), 159-251.

O'Brien, William D. and Floyd Dunn, "An early history of high-intensity focused ultrasound" *Phys. Today* 2015, 68(10), 40-45.

Prieur et al., "Observation of a cavitation cloud in tissue using correlation between ultrafast ultrasound images" *IEEE Trans. Ultrasan., Ferroelect., Freq. Contr.* 62, 1256-1264.

Radhakrishnan et al., "Relationship between cavitation and loss of echogenicity from ultrasound contrast agents" *Phys. Med Biol.* 2013, 58(18), 6541-6563.

Raymond et al., "Loss of gas from echogenic liposomes exposed to pulsed ultrasound" *Phys Med Biol.* 2016, 61(23), 8321-8339.

(56) References Cited

OTHER PUBLICATIONS

Rosnitskiy et al., "Design of HIFU Transducers for Generating Specified Nonlinear Ultrasound Fields" *IEEE Trans. Ultrasan., Ferroelect., Freq. Contr.* 2017, 64(2), 374-390.
Rosnitskiy et al., "On the possibility of using multi-element phased arrays for shock-wave action on deep brain structures" *Acoustical Physics* 2017, 63, 531-541.
Schuster et al., "Histotripsy Treatment of Benign Prostatic Enlargement Using the Vortx $R_x$ System: Initial Human Safety and Efficacy Outcomes" *Urology* 2018, 114, 184-187.
Shi et al., "Integrated histotripsy and bubble coalescence transducer for thrombolysis" *Ultrasound Med Biol.* 2018, 44(12), 2697-2709.
Shi et al., "Integrated Histotripsy and Bubble Coalescence Transducer for Rapid Tissue Ablation" *IEEE Trans. Ultrasan., Ferroelect., Freq. Contr.* 2018, 65(10), 1822-1831.
Szabo, Thomas. *Diagnostic Ultrasound Imaging: Inside Out (Biomedical Engineering).* Academic Press, 2004.
Vlaisavljevich et al. "Image-Guided Non-Invasive Ultrasound Liver Ablation Using Histotripsy: Feasibility Study in an In Vivo Porcine Model" *Ultrasound in Medicine & Biology* 2013, 39(8), 1398-1409.
Vlaisavljevich et al., "Effects of tissue stiffness, ultrasound frequency, and pressure on histotripsy-induced cavitation bubble behavior" *Phys. Med Biol.* 2015, 60(6), 2271-2292.
Wang eta al., "An Efficient Treatment Strategy for Histotripsy by Removing Cavitation Memory" *Ultrasound in Medicine & Biology* 2012, 38(5), 753-766.
Xu et al., "Optical and acoustic monitoring of bubble cloud dynamics at a tissue-fluid interface in ultrasound tissue erosion" *J Acoust Soc Am.* 2007, 121(4), 2421-2430.

\* cited by examiner
† cited by third party

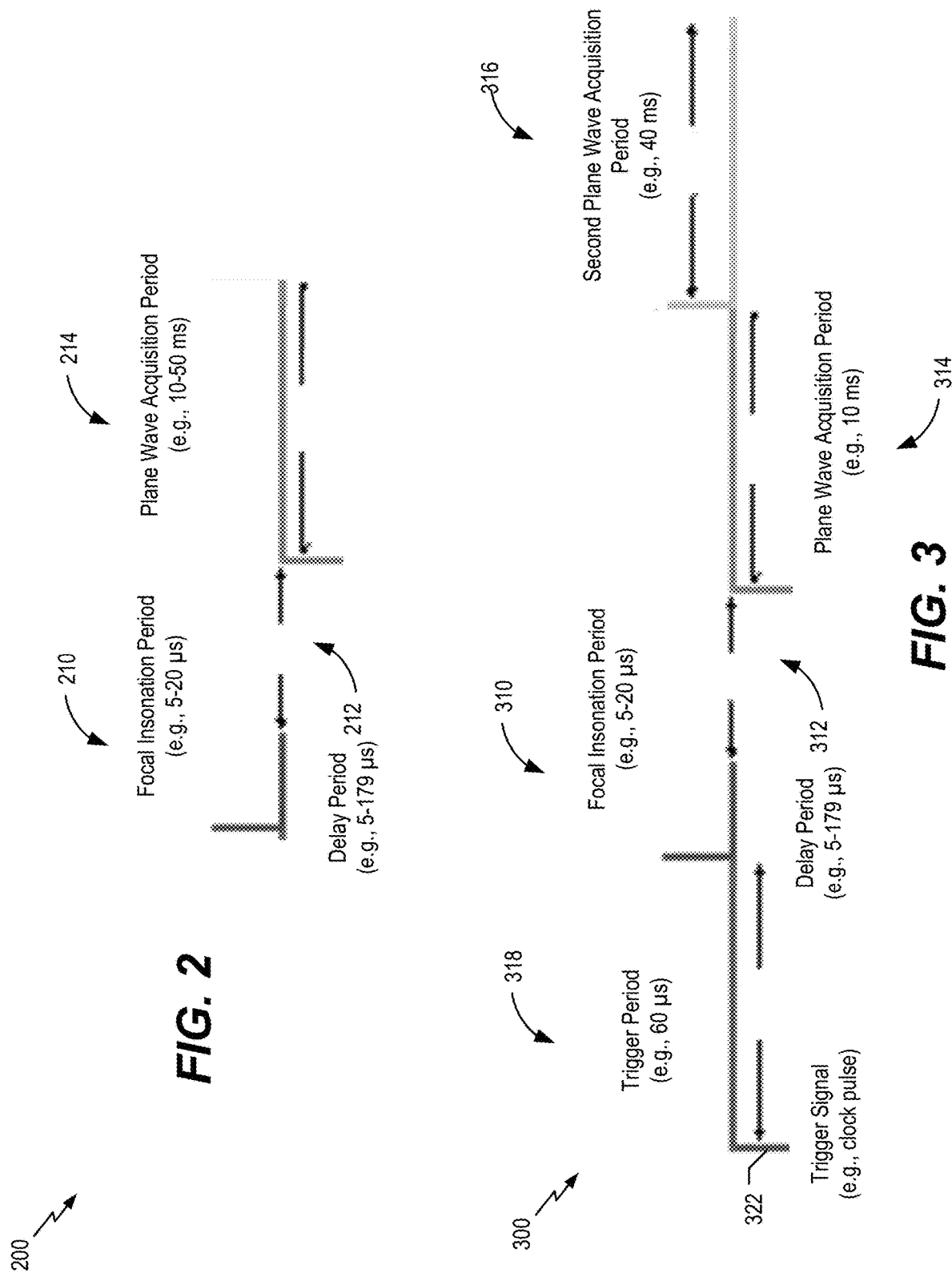

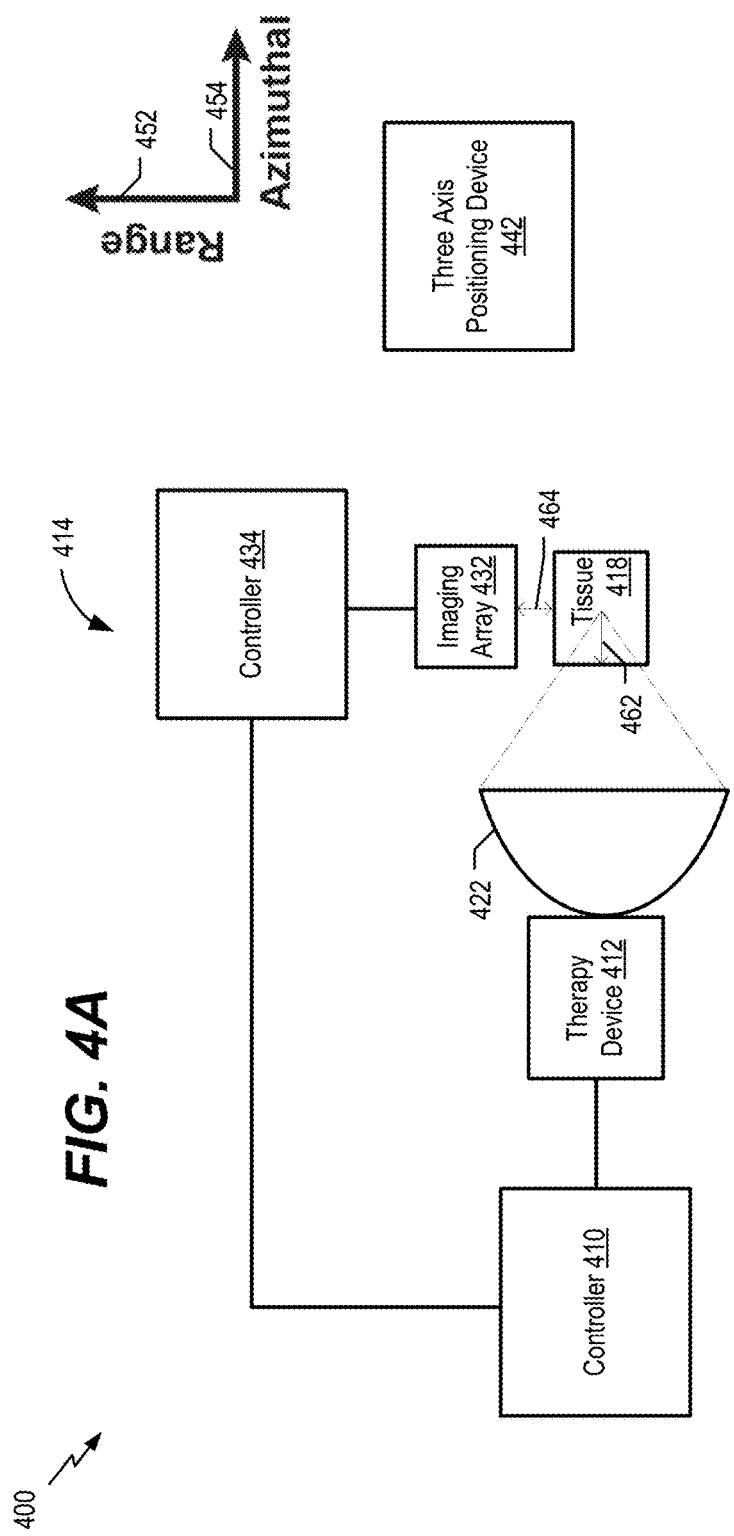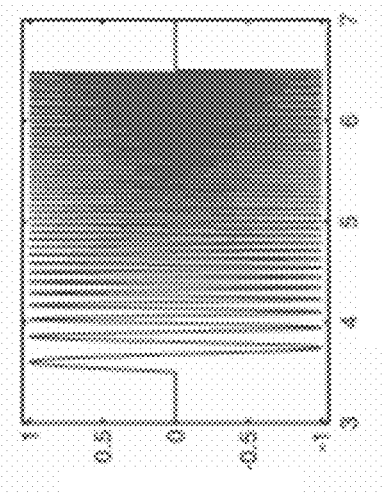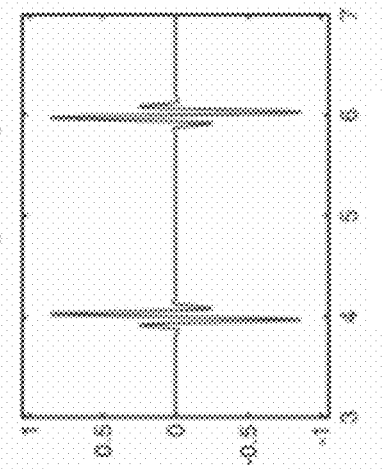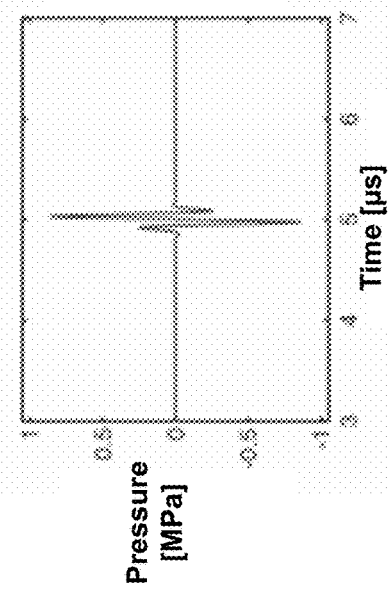

FIG. 9A
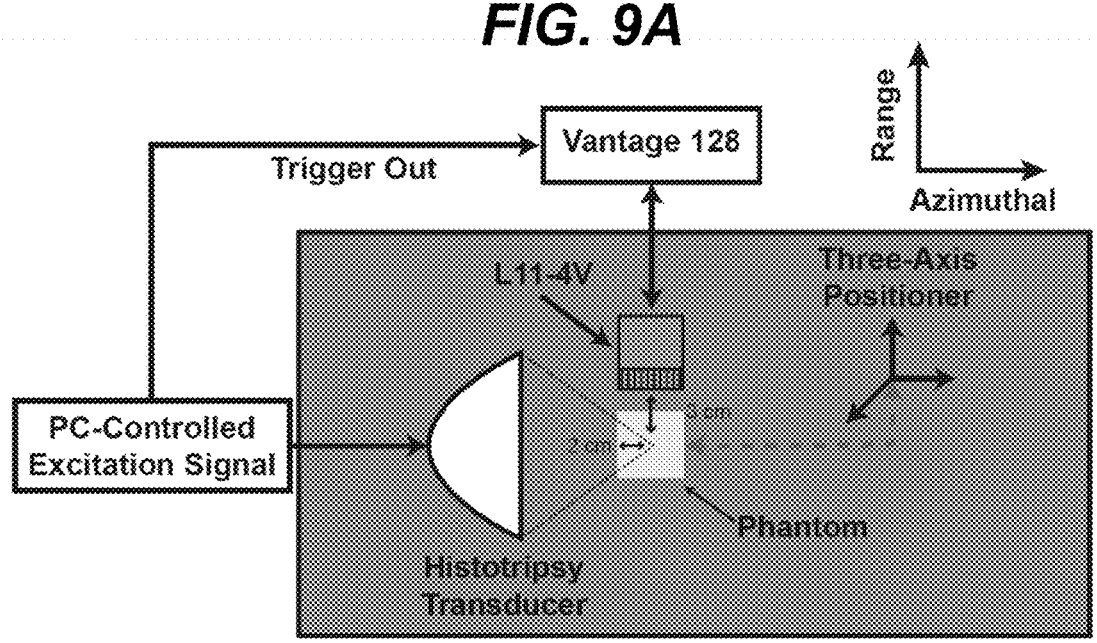
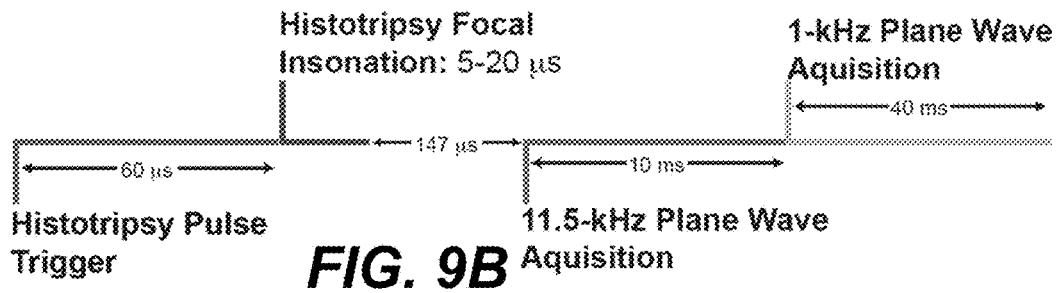
FIG. 9B
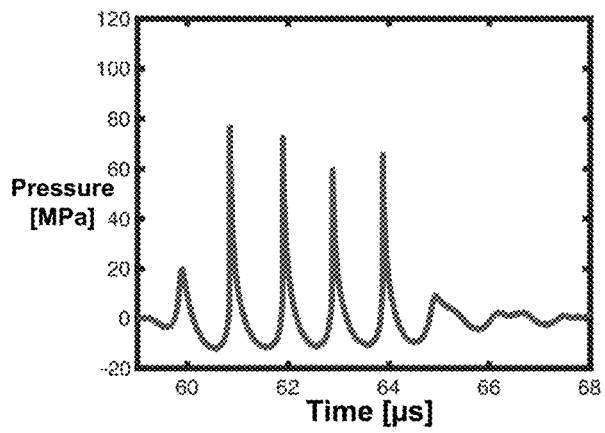
FIG. 9C
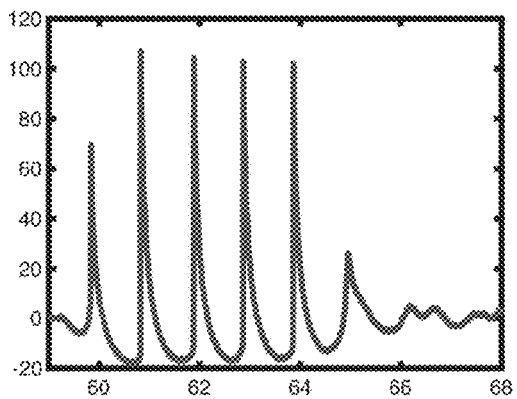
FIG. 9D

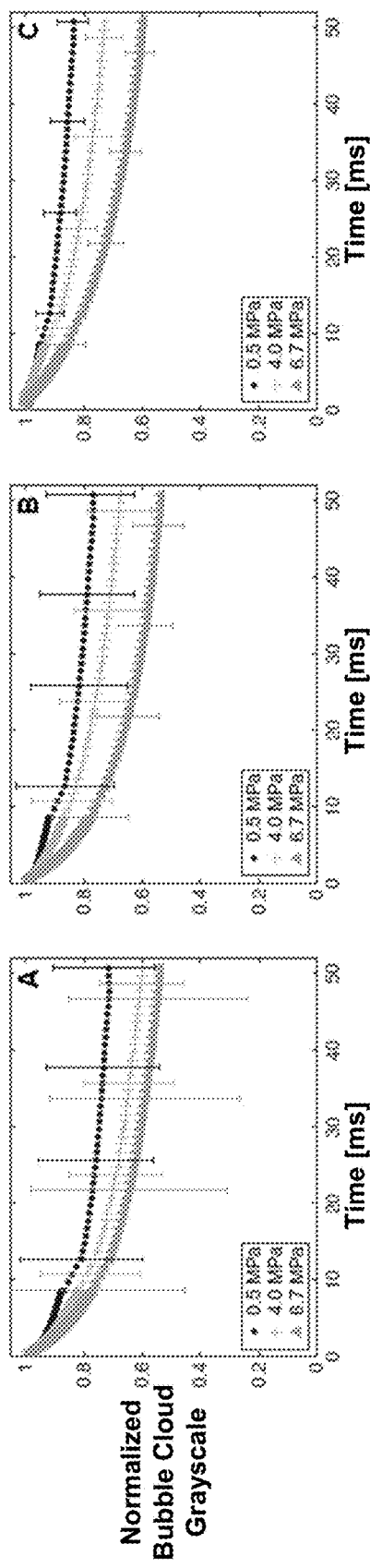
FIG. 16
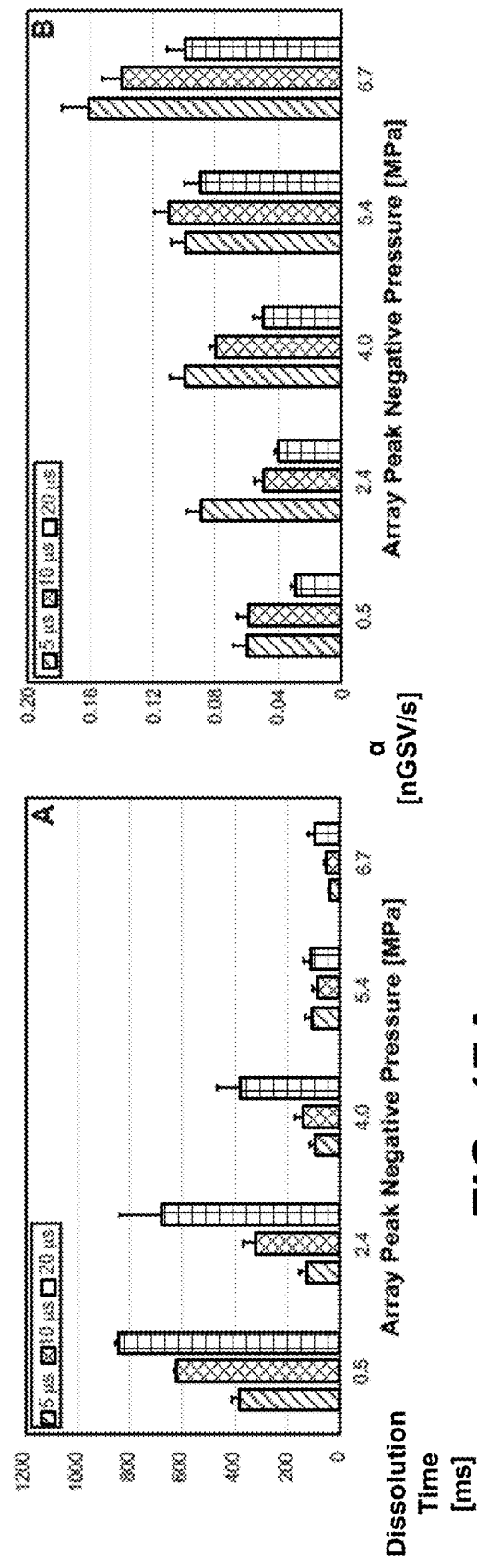
FIG. 17A
FIG. 17B

APPARATUS, SYSTEM, AND METHOD FOR MECHANICAL ABLATION WITH THERAPEUTIC ULTRASOUND

RELATED APPLICATIONS

This application claims priority to and the benefit of U.S. Provisional Patent Application No. 62/814,570, entitled "Apparatus, System, And Method For Mechanical Ablation With Therapeutic Ultrasound" and filed on Mar. 6, 2019.

GOVERNMENT LICENSE RIGHTS

This invention was made with government support under grant number R01 HL133334 awarded by the National Institutes of Health. The government has certain rights in the invention.

TECHNICAL FIELD

Aspects of the present disclosure relate generally to therapeutic ultrasound, such as histotripsy, and more specifically, but not by way of limitation, to therapeutic ultrasound bubble cloud control.

BACKGROUND

Focused ultrasound therapies are a noninvasive means to ablate tissue. Histotripsy is an ablative form of therapeutic ultrasound under development for the treatment of several pathological conditions, such as symptoms of benign prostatic hyperplasia (symptoms from an enlarged prostate). Histotripsy is a focused ultrasound therapy that utilizes short ultrasound pulses with sufficient tension to nucleate (e.g., grow) bubble clouds that impart strain to the surrounding tissues. Tissue is not damaged directly by the acoustic field of ultrasound therapy, but through the formation and mechanical activity of the bubble clouds generated within a focal region of the ultrasound waves. Once bubble activity is above a threshold, target tissue is liquefied.

Histotripsy treatment efficacy is dependent on sufficient bubble activity throughout the focal zone. Tracking the mechanical activity of the bubble clouds is used for assessing treatment efficacy. Thus, image guidance techniques focus on quantifying the degree of bubble activity. This is typically done through the visualization of hyperechoic bubble clouds on B-mode images or diffusion-weighted MR sequences, or spatially mapping acoustic emissions with passive cavitation imaging.

Additionally, bubble clouds, such as residual bubble clouds, that persist during the application of ablative forms of focused ultrasound reduce the treatment efficacy. Some other treatment methods use pulses ("coalescing pulses") to coalesce residual bubbles (i.e., join two bubbles to make one larger bubble or two conjoined bubbles), causing a portion of the residual bubbles to float out of the focal plane of the therapeutic ultrasound field by the increase in buoyancy. While such methods are sufficient for fluid-based applications and removing residual bubbles from bubble clouds between a fluid and tissue, the solid structure of soft tissue mitigates buoyancy forces within tissue. Thus, such coalescing pulses are not suitable for removing residual bubble from bubble clouds within tissue.

Furthermore, such coalescing pulses of prior bubble modulation methods cannot be utilized in conjunction with diagnostic ultrasound imaging to assess the presence of the residual bubble clouds at the fluid tissue interface. To illustrate, the coalescing pulses prevent or interfere with pulses of diagnostic ultrasound imaging such that the presence of the residual bubble cloud cannot be acquired during the application of the pulses of due to constructive interference between the imaging ultrasound pulses and the bubble coalescing pulses. Thus, with current methods real-time feedback and bubble modulation or control cannot be performed at the same time. Therefore, real-time feedback of the efficacy of bubble modulation (e.g., bubble deletion) is not possible with current methods.

Accordingly, to assess efficacy of the above bubble modulation methods intermittent assessment of the presence of residual bubbles is performed between therapy sessions. To illustrate, the therapy system stops applying the pulses used to coalesce bubbles to image the bubble cloud with conventional diagnostic ultrasound. Additionally, because no bubble modulation is being applied during ultrasound imaging, therapeutic ultrasound may also be stopped or reduced otherwise the bubble cloud may grow or persist and interfere with treatment.

Therefore, conventional methods are not able to modulate bubble clouds in tissue. Additionally, conventional methods are not able to perform real-time monitoring of bubble clouds while or in conjunction with bubble modulation methods such that an efficacy of treatment, bubble control/modulation, or both can be assessed and/or adjusted during treatment.

SUMMARY

This disclosure describes devices, systems, and methods related to therapeutic ultrasound with in tissue bubble cloud control, referred to as bubble cloud modulation. An exemplary therapeutic ultrasound system (e.g., histotripsy system) may include a transducer (e.g., histotripsy transducer), an ultrasound imaging device (e.g., plane wave B-mode ultrasound imaging device), and a controller. B-mode corresponds to brightness modulation or modulated ultrasound methods. Application of plane wave ultrasound causes the bubbles from bubble clouds within the tissue to diffuse gas from the bubble into tissue, rather than coalesce, and enables bubble cloud modulation or control within the tissue, and the plane wave ultrasound can simultaneously be used to produce ultrasound images. Thus, the devices, systems, and methods described herein can modulate bubble clouds within tissue. Additionally, the devices, systems, and methods described herein are able to perform real-time (e.g., during treatment) monitoring of bubble clouds and the efficacy of the bubble control/modulation. Accordingly, an efficacy of treatment, bubble control/modulation, or both, can be assessed and/or adjusted during treatment, which improves treatment efficacy and patient outcomes.

Additionally, plane wave ultrasound (e.g., plane wave B-mode ultrasound) utilizes a plurality or all elements of the imaging device in parallel for image acquisition, capturing the bubble cloud at a single instance in time. The short acquisition time, as compared to standard B-mode imaging, allows analysis of the bubble cloud at frame rates in excess of 10 kHz. Standard B-mode imaging sequences require several milliseconds to execute, and the bubble cloud may undergo significant changes over the course of image acquisition.

While plane wave imaging may not track volumetric oscillations of bubbles at therapeutically relevant frequencies, it is sufficient to assess passive dissolution of bubble clouds to determine efficacy of bubble modulation. In addition to monitoring bubble hyperechogenicity, high acoustic output pulses from plane wave B-mode sequences can destroy bubble nuclei present in the imaging plane and mitigate residual bubble clouds.

An exemplary sequence for applying therapy pulses and imaging/modulation pulses may include interleaving the therapy pulses and the imaging/modulation pulses such that the imaging/modulation pulses do not constructively interfere with therapy pulses. In some implementations, two different imaging/modulation pulses are applied after a therapy pulse. In a particular example, a relatively higher frequency imaging/modulation pulse is applied first and a relatively lower frequency imaging/modulation pulse is applied second. Such a configuration may enable the system to image tissue more quickly after a therapy pulse.

In some implementations, the system includes a controller to adjust the imaging device. Adjusting the imaging device, whose signal also modulate the residual bubble clouds, can enable the system to perform real-time, i.e., during treatment, adjustments to the plane wave ultrasound pulses used for imaging and for bubble modulation. Accordingly, reduced bubble clouds increases treatment uniformity and efficacy, and thus increases patient outcomes.

Additionally, or alternatively, the controller adjusts the transducer or a signal provided to the transducer. Adjusting the transducer, whose signal generates the bubble clouds and activates the bubble clouds to ablate tissue, can enable the system to perform real-time, i.e., during treatment, adjustments to the treatment pulses used for forming bubble clouds and ablating tissue with the bubble clouds. Accordingly, the bubble clouds can be controlled during treatment and the interaction of the bubble cloud and tissue can be controlled to increase treatment uniformity and efficacy, and thus increase patient outcomes.

Therefore, the devices, systems, and methods described herein able to perform real-time (e.g., during treatment) monitoring of in-tissue bubble clouds and the efficacy of in-tissue bubble control/modulation. As compared to prior methods which use ultrasound imaging, the plane wave B-mode imaging described herein is faster and can produce an image which captures residual bubble clouds in tissue. Additionally, the plane wave B-mode imaging pulses are configured to cause bubbles to diffuse into tissue, as compared to prior art pulses configured to coalesce bubbles on a fluid/tissue interface to remove the bubbles through buoyancy (i.e., floating to a surface of the fluid and away from the fluid/tissue interface). Thus, an efficacy of treatment, bubble control/modulation, or both, can be assessed and/or adjusted during treatment. Accordingly, the devices, systems, and methods described herein enable improved treatment efficacy and patient outcomes.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically. Additionally, two items that are "coupled" may be unitary with each other. To illustrate, components may be coupled by virtue of physical proximity, being integral to a single structure, or being formed from the same piece of material. Coupling may also include mechanical, thermal, electrical, communicational (e.g., wired or wireless), or chemical coupling (such as a chemical bond) in some contexts.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. As used herein, the term "approximately" may be substituted with "within 10 percent of" what is specified. Additionally, the term "substantially" may be substituted with "within [a percentage] of" what is specified, where the percentage includes 0.1, 1, or 5 percent; or may be understood to mean with a design, manufacture, or measurement tolerance. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including"). As a result, an apparatus that "comprises," "has," or "includes" one or more elements possesses those one or more elements, but is not limited to possessing only those one or more elements. Likewise, a method that "comprises," "has," or "includes" one or more steps possesses those one or more steps, but is not limited to possessing only those one or more steps.

Any aspect of any of the systems, methods, and article of manufacture can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. The feature or features of one embodiment may be applied to other embodiments, even though not described or illustrated, unless expressly prohibited by this disclosure or the nature of the embodiments.

Some details associated with the aspects of the present disclosure are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE DRAWINGS

A further understanding of the nature and advantages of the present disclosure may be realized by reference to the following drawings. The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 2 is a timing diagram of an example of operation of a therapy system;

FIG. 3 is a timing diagram of another example of operation of a therapy system;

FIG. 4A is a side view of an example of a therapy system;

FIGS. 4B-4D are each a diagram illustrating an exemplary pulse scheme for plane wave imaging pulses;

FIG. 9A is a side view of experimental set up for histotripsy bubble cloud generation in the tissue mimicking phantom;

FIG. 9B is an exemplary timing diagram for the acquisition of high frame rate plane wave B-mode images following the histotripsy focal insonation;

FIG. 9C is an exemplary diagram illustrating pressure during histotripsy focal insonation;

FIG. 9D is another exemplary diagram illustrating pressure during histotripsy focal insonation;

FIG. 16 is a series of diagrams illustrating normalized bubble cloud grayscale values as a function of time for different peak negative pressure histotripsy pulses;

FIG. 17A is a diagram illustrating complete bubble cloud dissolution time as a function of peak negative pressure of the plane wave imaging pulse;

FIG. 17B is a diagram illustrating a fitting parameter of bubble cloud dissolution calculations as a function of peak negative pressure of the plane wave imaging pulse;

DETAILED DESCRIPTION

Figure 1:
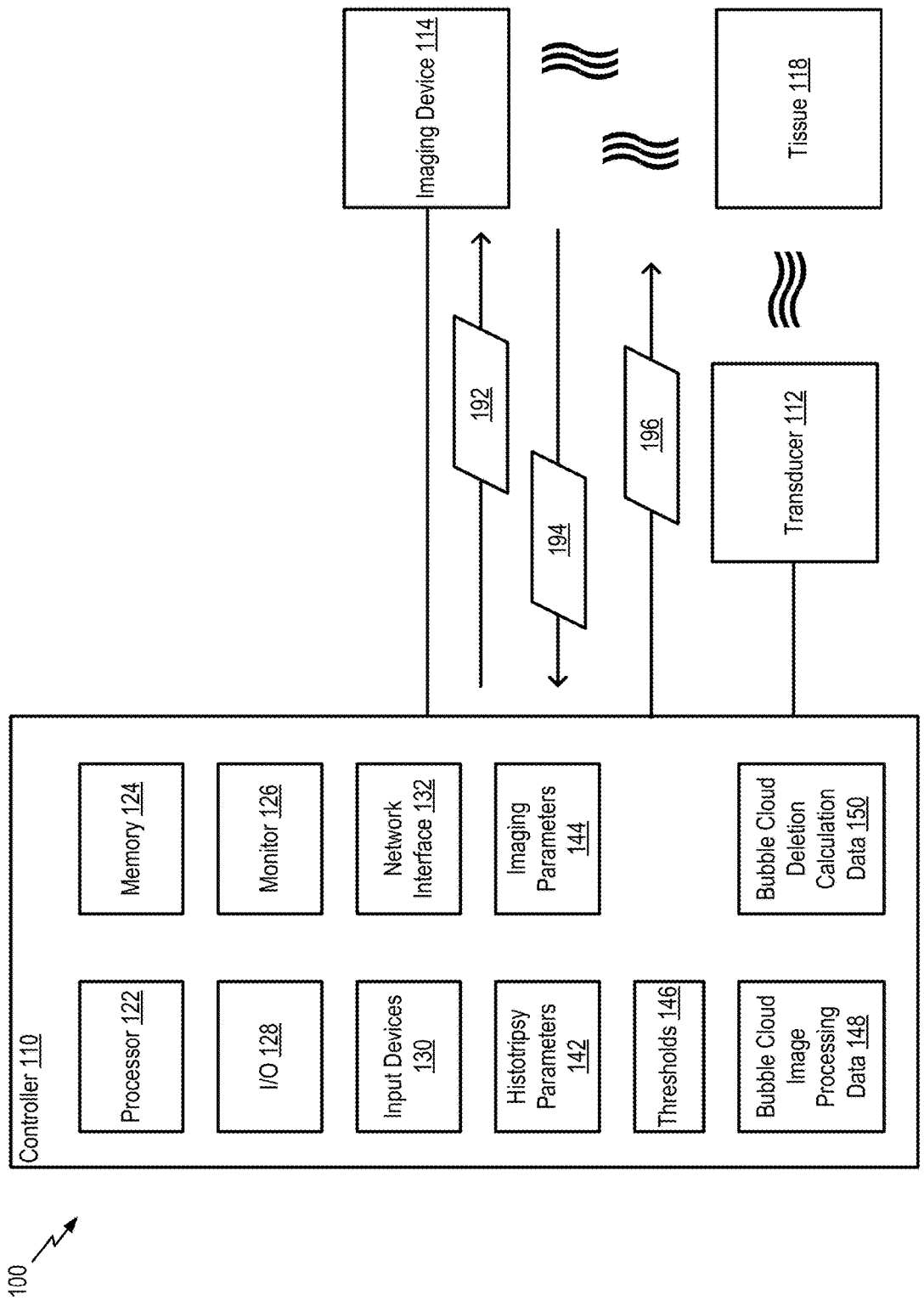
FIG. 1 is a block diagram of an example of a therapy system.

FIG. 1 illustrates a block diagram of an example of a therapy system 100 (referred to herein as "system 100") for providing therapeutic ultrasound or histotripsy therapy and bubble cloud modulation or control. System 100 includes a controller 110 (e.g., a computer), a transducer 112, and an ultrasound imaging device 114 (e.g., a plane wave B-mode ultrasound device). System 100 is configured to provide therapeutic ultrasound or histotripsy therapy to tissue 118, such as ablate a portion of tissue 118. One exemplary tissue that can be ablated by system 100 is prostate tissue. Another exemplary use for system 100 is ablation of a thrombus (aka a blood clot) within tissue 118. The thrombus may be in veins, arteries, or superficial (i.e., underneath skin). To illustrate, controller 110 may send activation signals 192 (e.g., trigger signals or clock pulses) to transducer 112 to provide and adjust histotripsy therapy to tissue 118. One such exemplary use of system 100 is as real-time feedback control of histotripsy therapy.

As illustrated in FIG. 1, the controller 110 includes a processor 122, a memory 124, a monitor 126, input/output (I/O) interfaces 128, input devices 130, and a network interface 132. The controller 110 is configured to control devices of system 100, such as the transducer 112 and the ultrasound imaging device 114. For example, the controller 110 sends signals to devices of system 100 to cause activation of and/or control of the device or a component thereof, as explained further herein.

The processor 122 is configured to execute instructions and is coupled to the memory 124. In some implementations, processor 122 may include or correspond to a microcontroller/microprocessor, a central processing unit (CPU), a field-programmable gate array (FPGA) device, an application-specific integrated circuits (ASIC), another hardware device, a firmware device, or any combination thereof. The processor 122 may be configured to execute instructions to initiate or perform one or more operations described with reference to FIGS. 1-4A, and/or one or more operations of the methods of FIGS. 5-8.

The memory 124, such as a non-transitory computer-readable storage medium, may include volatile memory devices (e.g., random access memory (RAM) devices), nonvolatile memory devices (e.g., read-only memory (ROM) devices, programmable read-only memory, and flash memory), or both. The memory 124 is configured to store instructions that when executed by the processor 122, cause the processor 122 to perform the operations described herein. For example, the processor 122 may perform operations as described with reference to FIGS. 1-4A and the methods of FIGS. 5-8. The memory 124 may be further configured to store data, such as data used to adjust operation of the transducer 112 and the ultrasound imaging device 114.

As illustrated in FIG. 1, the memory 124 is configured to store histotripsy therapy parameters 142, imaging parameters 144, thresholds 146, bubble cloud image processing data 148, bubble cloud deletion calculation data 150, or a combination thereof. The histotripsy therapy parameters 142 include data defining parameters or variables of the ultrasonic sound waves used in providing therapy. As illustrative, non-limiting examples, the histotripsy therapy parameters 142 include frequency parameters, pulse length/duration parameters, exposure time parameters, intensity parameters, focus area parameters, etc. The intensity parameters may include or correspond to a negative pressure, a peak negative pressure, a focal peak negative pressure, a positive pressure, a peak positive pressure, and a focal peak positive pressure. The intensity parameters may be original (i.e., output) or derated (i.e., attenuated). Derated parameters have a factor applied to the original acoustic output parameters intended to account for ultrasonic attenuation of tissue 118 between the source and a particular location in the tissue 118, i.e., a therapy site.

The imaging parameters 144 includes data defining parameters or variables of the ultrasonic sound waves used in imaging and/or bubble modulation. As illustrative, non-limiting examples, the imaging parameters 144 include frequency parameters, pulse length/duration parameters, exposure time parameters, intensity parameters, focus area parameters, etc.

The thresholds 146 include data indicating thresholds for histotripsy therapy, imaging, bubble modulation, or a combination thereof. As illustrative, non-limiting examples, the thresholds 146 include thresholds for histotripsy therapy parameters, thresholds for imaging parameters, bubble size thresholds, bubble cloud deletion rate thresholds.

The bubble cloud image processing data 148 includes instructions, such as a program or an application, configured to process raw image data or binarized image data. For example, the bubble cloud image processing data 148 receives sensor data from imaging device 114, such as data representing intensity values of backscatter signal, and produces an image (ultrasonic image) based on the data. The image may be in grayscale. As another example, the bubble cloud image processing data 148 receives a grayscale image (e.g., FIG. 10A) from imaging device 114 and generates a B-mode (brightness modulated) image (e.g., FIG. 10B) based on the grayscale image.

The bubble cloud deletion calculation data 150 includes instructions, such as a program or an application, configured to analyze raw image data or binarized image data to generate bubble cloud deletion parameters, such as bubble cloud movement, bubble cloud reduction in size, bubble deletion rate, bubble size, etc.

The controller 110 may include or correspond to an electronic device, such as a communications device, a mobile phone, a cellular phone, a satellite phone, a computer, a server, a tablet, a portable computer, a display device, a media player, or a desktop computer. Additionally, or alternatively, the controller 110 may include any other device that includes a processor or that stores or retrieves data or computer instructions, or a combination thereof. In some implementations, the controller 110 includes a graphics processor, such as a dedicated graphics card or graphics processing unit (GPU).

The monitor 126 is configured to display information from components of the system, such as information from the transducer 112 and/or the imaging device 114. The monitor 126 may display image data, bubble cloud data, bubble cloud deletion rate data, adjustment instruction data, etc.

The I/O interface 128 includes or corresponds to an interface and bus for receiving and sending data to local devices and other local computers. For example, the I/O interface 128 may include or correspond to a Universal Serial Bus (USB) interface.

The one or more input devices 130 may include a mouse, a keyboard, a joystick, a display device, other input devices, or a combination thereof, and may be coupled to the controller 110 via the I/O interface 128. In some implementations, the controller 110 (e.g., processor 122) generates and sends trigger pulses or adjustment commands responsive to receiving one or more user inputs from the one or more input devices 130 via the I/O interface 128.

The network interface 132 includes or corresponds to a networking interface and bus for receiving and sending data to other computers or devices over a network, such a local area network. For example, network interface 132 may include a transmitter, a receiver, or a combination thereof (e.g., a transceiver), and may enable wired communication, wireless communication, or a combination thereof, with the transducer 112, the imaging device 114, or both. Alternatively, the controller 110 communicates with the transducer 112, the imaging device 114, or both, via the I/O interface 128.

The controller 110 is configured to send activation signals 192 (e.g., trigger signals or clock pulses) to the transducer 112, the imaging device 114, or both, to provide and adjust histotripsy therapy to tissue 118. For example, the controller 110 may include a clock pulse generator configured to generate clock pulses used to generate activation signals 192. The activation signals 192 (e.g., clock pulses or trigger signals) cause the transducer 112, the imaging device 114, or both, to emit ultrasonic waves. In other implementations, the activation signal 192 includes or correspond to a control signal, i.e., the activation signal 192 is a control signal (e.g., an excitation signal) that drives the transducer 112.

The controller 110 is configured to receive data and messages from the transducer 112, the imaging device 114, or both, such as a data 194 (e.g., raw image data, a bubble cloud image data, or bubble cloud deletion rate). Additionally, the controller 110 is configured to send commands to the transducer 112, the imaging device 114, or both, such as an adjustment signal 196 (e.g., an adjustment control signal or command), responsive to and based on the data 194. In some implementations, the controller 110 is further configured to send and receive additional data with the transducer 112, the imaging device 114, or both, as described further with reference to FIG. 2 and FIGS. 5-8.

In other implementations, functions of the controller 110 may be distributed. For example, each of the transducer 112 and the imaging device 114 may include a corresponding controller, similar to controller 110. The corresponding controllers may be coupled or linked to each other to provide synchronous timing signals to the transducer 112 and the imaging device 114. Distributed control is described further with reference to FIG. 4A.

The transducer 112 includes or corresponds to a histotripsy transducer or a therapeutic ultrasound device. The transducer 112 is configured to generate and emit ultrasonic sound waves, i.e., an ultrasound signal or ultrasound waves towards tissue 118 responsive to receiving activation signals 192 from the controller 110. As the ultrasonic sound waves impinges on the tissue 118, portions of the ultrasonic sound waves are reflected, absorbed, and transmitted and bubbles form in tissue 118. It is believed that the bubbles are generated in the extracellular fluid or water space of tissue 118. The transducer 112 is configured to generate pulses of ultrasonic sound waves (also referred to as therapy pulses, insonation pulses, therapy signals, etc.) such that the pulses of cause the bubble cloud to form and the bubble cloud to ablate a portion of tissue 118 by mechanically interacting with cells of tissue 118.

The transducer 112 converts an electrical signal into ultrasonic sound waves (i.e., mechanical waves). Ultrasonic sound waves include sound waves having a frequency above 20 thousand cycles per second (20,000 Hz) or the generally above the highest frequency which humans can hear. In some implementations, the transducer 112 generates its control signal used to generate the ultrasonic sound waves. In other implementations, transducer 112 receives a control signal from the controller 110 and generates the ultrasonic sound waves based on the received control signal.

As an illustrative, non-limiting example, the transducer 112 includes a 1-MHz ultrasound transducer and has an 8-element annular array with a 10-cm aperture (e.g., outer diameter) and 9-cm focal length, such as a transducer from Imasonic, Voray sur l'Ognon, France. An annular array includes elements (e.g., piezoelectric crystals, such as quartz) arranged in concentric rings with different frequencies of sound produced by each element or ring. The transducer array elements may be simultaneously driven in parallel. As an illustrative, non-limiting example, the transducer 112 includes a custom designed and built class D amplifier and matching network as in Hall and Cain 2006. In other implementations, the transducer 112 includes a linear array or has another shape.

In some implementations, the transducer 112 may be calibrated in water. For example, the transducer 112 may be calibrated in water at a focus for peak negative pressures up to 18.3 MPa with a fiber optic hydrophone, such as FOPH 2000, RP Acoustics, e.K., Leutenbach, Germany according to the method of Bader et al. 2016b. As an illustrative, non-limiting example, peak negative pressure may be estimated following the analytical methods provided in Maxwell et al. (2013). In other implementations, the transducer 112 may be directly calibrated for peak pressures (e.g., positive or negative).

The imaging device 114 includes or corresponds to an ultrasound imaging device, such as a plane wave B-mode imaging device. B-mode refers to brightness modulated. As an illustrative, non-limiting example, the imaging device 114 includes or corresponds to an L11-4v imaging array, made by Verasonics, Inc., Kirkland, WA, USA, and is driven by a research ultrasound scanner Vantage 128, made by Verasonics, Inc.

The imaging device 114 is configured to generate and emit ultrasonic sound waves, i.e., an ultrasound signal or ultrasound pulse, responsive to receiving activation signals 192 from the controller 110. As the ultrasonic sound waves impinge on the tissue 118, a portion of the ultrasonic sound waves is reflected back towards the imaging device and results in a backscatter signal. The imaging device 114 is configured to receive the backscatter signal and to generate image data based on the received backscatter signal. The imaging device 114 is configured to send the image data to the controller 110.

Operations of system 100 are described further with reference to FIGS. 2 and 3 in detail with reference to FIGS. 5-8. Additionally, an exemplary configuration and layout of system 100 is described with reference to FIG. 4A. System 100 is capable of providing real-time feedback of bubble clouds in tissue during therapeutic ultrasound. For example, plane wave ultrasound waves applied intermittently/interleaved between pulses of therapy produce a backscatter signal that is capable of imaging residual bubble clouds within tissue, as opposed to bubble clouds formed on surface or interface between fluid and tissue. Accordingly, the therapeutic device can be controlled based on feedback of residual bubble clouds within tissue determined during operation so that the therapy can be improved (e.g., optimized) during a treatment session and complications can be reduced. System 100 is capable of using imaging waves to modulate or control bubble clouds in tissue during therapeutic ultrasound. For example, the plane wave ultrasound waves which produce the backscatter signal used for imaging also modulate the bubble cloud (e.g., an original or mother bubble cloud). Accordingly, the therapeutic device is more effective because modulating the bubble cloud reduces the presence and intensity of residual bubble clouds and their interference with treatment. Thus, system 100 solves many of the shortcomings of conventional systems and methods for therapeutic ultrasound.

Referring to FIG. 2, a timing diagram 200 of operation of a therapy system, such as system 100, is illustrated. As illustrated in FIG. 2, timing diagram 200 illustrates a focal insonation period 210, a delay period 212, and a plane wave acquisition period 214, which together form a treatment cycle. The treatment cycle may be repeated numerous times to form a therapy session.

The focal insonation period 210 includes or corresponds to a time period or duration where histotripsy therapy or ultrasound therapy is applied to tissue, e.g., tissue 118. As explained above, application of histotripsy therapy or ultrasound therapy may cause bubbles to form in tissue 118 and may cause the bubbles to ablate a portion of tissue 118. The portion of tissue 118 ablated may include or correspond to cells near a focal or focus region of application of ultrasound signals. In some implementations, the focal insonation period 210 includes a single pulse of ultrasound therapy.

A pulse (or pulses) of the focal insonation period 210 may have a pulse length (duration) between 3-40 µs in some implementations. In a particular implementation, a pulse of the focal insonation period 210 has a pulse length of 5-20 µs. Exemplary pulse lengths include pulse lengths of 5 µs, 10 µs, and 20 µs. Therapy ultrasound waves of a pulse (or pulses) of the focal insonation period 210 may have a frequency (e.g., fundamental frequency) of 800 kHz to 1200 kHz in some implementations. In a particular implementation, therapy ultrasound waves of a pulse of the focal insonation period 210 have a frequency 1 of MHz.

Additionally, or alternatively, pulses of the focal insonation period 210 may have a pulse repetition frequency of 10-30 Hertz. In a particular implementation, the pulses of the focal insonation period 210 have a pulse repetition frequency of about 20 Hertz, i.e., 20 times or pulses a second. Tissue exposure times are based on pulse length and pulse repetition frequency, and exemplary tissue exposure time include 10, 20, and 40 ms. In some implementations, tissue exposure times may be 5 ms to 60 ms.

In some implementations, a peak negative pressure of a pulse of the focal insonation period 210 is between 10-20 MPa. In particular implementations, the peak negative pressure is between 15-20 MPa or is greater than 15 MPa. Exemplary peak negative pressures include 14.5, 16.1, and 18.3 MPa.

In some implementations, a derated focal peak negative pressure of a pulse of the focal insonation period 210 is between 10-30 MPa. In particular implementations, the derated focal peak negative pressure is between 12-23 MPa or is greater than 12 MPa. Exemplary derated focal peak negative pressures include 12, 18, and 23 MPa.

In some implementations, a derated peak positive pressure of pulses of the focal insonation period 210 are between 50-150 MPa. In particular implementations, the derated peak positive pressure is between 77-105 MPa or is greater than 77 MPa. Exemplary derated peak positive pressures include 77, 105, 123 MPa.

The delay period 212 includes or corresponds to a time period or duration where no ultrasound is being direction at the tissue. Such a time period may enable improved imaging and reduced constructive interference between therapy ultrasound signals and imaging/bubble modulation ultrasound signals.

The plane wave acquisition period 214 include or corresponds to a time period or duration where plane wave ultrasound signals are applied to tissue, e.g., tissue 118, where backscatter signals generated therefrom are processed, or both. In some implementations, plane wave ultrasound signals may be applied to tissue, such as for bubble cloud control or modulation, longer than or without processing the backscatter signals. As an illustrative example, plane wave ultrasound signals may be sent during the entire plane wave acquisition period 214 and images are only captured during a portion of plane wave acquisition period 214, such as a second half. As an additional example, the delay period 212 may be reduced or eliminated to add additional plane wave ultrasound to control bubble modulation. In some implementations, the plane wave acquisition period 214 includes a multiple pulses and multiple corresponding backscatter signals. Thus, in such implementations, multiple images (e.g., image frames) are captured during a single plane wave acquisition period 214.

In some implementations, a peak negative pressure of pulses of the plane wave acquisition period 214 are between 10 kPA to 10 MPa. In particular implementations, the peak negative pressure is between 420 kPA to 6.7 MPa or is greater than 420 kPA.

Additionally, or alternatively, ultrasound waves of pulses of the plane wave acquisition period 214 may have a frequency (e.g., fundamental frequency) of 800 kHz-10 MHz. In a particular implementation, ultrasound waves of the pulses of the plane wave acquisition period 214 have a frequency of about 6.25 MHz. In another particular implementation, ultrasound waves of the pulses of the plane wave acquisition period 214 have a frequency of about 1 MHz.

In a particular implementation, the delay period is about 147-179 µs and an imaging device (e.g., 114) starts capturing images 147-179 µs after the focal insonation period 210. Additional, plane wave types and plane wave acquisition periods may be used in other implementations, as described with reference to FIG. 3.

Referring to FIG. 3, a timing diagram 300 of operation of a therapy system, such as system 100, is illustrated. As illustrated in FIG. 3, timing diagram 300 illustrates a focal insonation period 310, a delay period 312, a first plane wave acquisition period 314, and a second plane wave acquisition period 316. The focal insonation period 310 may include or correspond to the focal insonation period 210, and the delay period 312 include or correspond to the delay period 212.

The first plane wave acquisition period 314 or the second plane wave acquisition period 316 may include or correspond to the plane wave acquisition period 214. As illustrated in FIG. 3, the first plane wave acquisition period 314 includes or corresponds to a high frame rate plane wave acquisition period and the second plane wave acquisition period 316 includes or corresponds to a low frame rate plane wave acquisition period, relative to one another. For example, the first plane wave acquisition period 314 may include or correspond to an 11.5 kHz plane wave acquisition period (e.g., 1000 frames per second), and the second plane wave acquisition period 316 may include or correspond to an 1 kHz plane wave acquisition period (e.g., 1000 frames per second). Alternatively, the first plane wave acquisition period 314 includes or corresponds to a low frame rate plane wave acquisition period and the second plane wave acquisition period 316 includes or corresponds to a high frame rate plane wave acquisition period, relative to one another.

In some implementations, the first plane wave acquisition period 314 is shorter (i.e., has a smaller or lesser duration) that the second plane wave acquisition period 316. For example, as illustrated in FIG. 3, a duration of the first plane wave acquisition period 314 is 10 ms, and a duration of the second plane wave acquisition period 316 is 40 ms. Alternatively, the first plane wave acquisition period 314 is longer (i.e., has a greater or larger duration) than the second plane wave acquisition period 316. In a particular implementation, the delay period 312 is about 147-179 µs and the first plane wave acquisition period 314 is about 10 ms, thus an imaging device (e.g., 114) starts capturing second images about 10.2 ms after the focal insonation period 310. Second images correspond to images generated based on a backscatter signal produced by second plane waves of the second plane wave acquisition period 314.

In some implementations, a plane wave acquisition period (e.g., 314, 316, or both) does not process backscatter signals and corresponds to a bubble control or modulation period only. Additionally, or alternatively, one or more of the plane wave acquisition periods (or a portion thereof) may not modulate or control (e.g., reduce an amount of and a size of) bubbles formed in the tissue from focal insonation (ultrasound therapy).

In some implementations, there may be an additional delay period (e.g., 312) between the first plane wave acquisition period 314 and the second plane wave acquisition period 316. Such a delay period may provide a clearer signal (e.g., increased signal to noise ratio) and reduce or prevent constructive interference between ultrasound waves of different types.

In some implementations, the periods 310-318 are initiated or triggered by a trigger signal 322 (i.e., a same signal). As an illustrative example, the trigger signal 322 includes or corresponds to the activation signal 192. In other implementations, each of the periods 310-318 are initiated or triggered by a corresponding activation signal (i.e., multiple activations are used to control timing).

This timing sequence illustrated in FIG. 3 may repeat for many cycles to form a therapy cycle or treatment session. For example, one therapy cycle or treatment session may include 2000 cycles depicted in FIG. 2 or 3. The process may be adjusted mid cycle or from cycle to cycle. For example, the timing of the signals may be adjusted by adjusting the trigger signal 322. As another example, image data may only be generated once every "N" number cycles. For example, backscatter signals are generated each plane wave acquisition period from the emitted ultrasound, but the backscatter signals are only received and/or processed once every 10 cycles, 200 cycles, etc., to form image data, bubble deletion rates, adjustments, or a combination thereof.

In a particular implementation, there is a delay between the trigger signal 322 an activation of focal insonation, i.e., start of period 318. The delay may be used to prevent constructive interference between imaging waves of a previous cycle and therapy waves of a next or current cycle or may represent the time it takes for signal propagation and processing by components.

The timing sequences illustrated in FIGS. 2 and 3 enable ultrasound diagnostic imaging during a treatment session. Additionally, the timing sequences enable bubble modulation with the ultrasound waves/signals/pulses, used for the ultrasound diagnostic imaging. Accordingly, a therapy system, such as system 100, includes benefits and advantages over conventional therapy systems because such a therapy system can modulate bubble clouds within tissue and can image bubble clouds in tissue in real-time (i.e., during treatment). Therefore, treatment efficacy and patient outcomes are increased.

Additionally, such real-time or in treatment feedback enables adjustment of the treatment or imaging during a session such that tissue ablation can be improved or optimized. Accordingly, treatment efficacy and patient outcomes are further increased over conventional methods which are not capable of modulating bubbles (in or outside of tissue) and providing real time in treatment feedback.

Referring to FIG. 4A, a side view of an example of therapy system 400 is illustrated. System 400 includes a controller 410, a therapy device 412, and an imaging device 414. System 400 may include or correspond to therapy system 100, and operate with timings described in FIGS. 2 and 3. The therapy device 412 includes a histotripsy transducer 422 (also referred to as "transducer 422") and the imaging device 414 includes an imaging array 432 and a controller 434. The therapy device 412 and/or the histotripsy transducer 422 may include or correspond to the transducer 112 of FIG. 1. As illustrated in the example of FIG. 4A, the transducer 422 is controlled by the controller 410, i.e., receives an excitation signal from the controller 410 which drives the transducer 422 to generate the therapy ultrasound signal/pulse. The therapy pulse generates or causes a bubble cloud within tissue 418. As multiple therapy pulses are applied, the bubble cloud grows in the azimuthal axis 454 and into a nearfield (leftward in FIG. 4A) relative to a focus of the transducer 422.

The imaging array 432 is configured to capture image data. In some implementations, the imaging array 432 is configured to capture backscatter signal intensity data. In some implementations, the imaging array 432 is a linear array. As illustrated in the example of FIG. 4A, the imaging array has a focus area width of 3 centimeters. In other implementations, the focus area and/or the width thereof of the imaging array 432 may be larger or smaller based on a size of a therapy site and the transducer 422.

The imaging array 432 may also be configured to generate and emit an image pulse signal, which is partially reflected by tissue 418 to create the backscatter signal. As an illustrative, non-limiting example, the imaging array 432 is configured to generate a 6.25 MHz imaging pulse.

The controller 434 is configured to control or "drive" the imaging array 432. In some implementations, the controller 434 is configured to process or partially process the image data. In other implementations, the controller 434 sends the image data (e.g., raw image data or intensity values) to the controller 410. The controller 434 may include components similar to controller 110.

As illustrated in FIG. 4A, the imaging array 432 of the imaging device 414 is oriented to monitor bubble cloud activity along a central axis (e.g., an azimuth/range plane of the imaging array as illustrated in FIG. 4A) of the histotripsy transducer 422. The histotripsy transducer 422 may have a 9-cm focal length and 10-cm outer diameter. The histotripsy transducer 422 may be placed into the tissue 418, adjacent to the 418, or oriented at the tissue 418. As illustrated in FIG. 4A, the histotripsy transducer 422 is positioned (i.e., located and oriented) such that a focus of the histotripsy transducer 422 is at a depth of 2 cm, 462, into the tissue in the azimuthal axis 454. A distance 464 between the imaging array 432 and the focus of the histotripsy transducer 422 is 3 cm in the range axis 452. The histotripsy transducer 422 and the imaging array 432 may be aligned confocally, i.e., a focus of each of the histotripsy transducer 422 and the imaging array 432 overlap each other (at least partially).

In some implementations, a focal distance of the transducer 422 is 60 mm or greater. In some such implementations, the focal distance of the transducer 422 is 2-3 times longer than a focal distance of the imaging array 432. Accordingly, an imaging pulse will be more attenuated by the tissue 418 than a therapy pulse.

In some implementations, the system 400 includes multiple imaging arrays. For example, each imaging array acquires image data in a fixed two-dimensional plane. Thus, to capture a larger portion of the volume of the bubble cloud, multiple imaging arrays may be positioned in parallel or angled from one another such that additional image "slices" of the bubble cloud are captured.

In some implementations, system 400 includes a three-axis positioning device or system, such as three axis positioning device 442. The three axis positioning device 442 is configured to determine, place, and/or orient the histotripsy transducer 422, the imaging array, 432 or both. In a particular implementation, the three axis positioning device 442 is configured to adjust a position or an orientation of the histotripsy transducer 422, the imaging array, 432 or both, during operation (e.g., during a treatment cycle or session). For example, the three axis positioning device 442 may adjust an orientation angle (e.g., by rotating or turning) of the histotripsy transducer 422 to adjust a focus of the histotripsy transducer 422, such as adjust where on the tissue 418 the focus of the histotripsy transducer 422 is located. In some implementations, the three axis positioning device 442 is further configured to adjust tissue 418, such as a patient including tissue 418. As an illustrative example, the three axis positioning device 442 includes or corresponds to one or more server motors and a servo motor controller, such as T-Cube DC Servo Motor Controller from by Thorlabs Inc., Newton, NJ, USA.

Referring to FIGS. 4B-4D, image pulsing schemes for plane wave acquisition periods, such as 214, 314, 316, are illustrated. The image pulses of the image pulsing schemes of FIGS. 4B-4D may be generated by the imaging device 114 or the imaging array 432. The image pulsing schemes are suitable for contrast specific imaging. Although three exemplary image pulsing schemes are illustrate, other image pulsing schemes are suitable for contrast specific imaging may be used in other implementations.

FIG. 4B illustrates a single repeating imaging pulse imaging scheme, such as a conventional or standard imaging pulse scheme. FIG. 4C illustrates a pulse inversion imaging scheme. In FIG. 4C, the pulse inversion imaging scheme includes a first pulse that has a first orientation or shape with respect to positive and negative pressure and includes a second pulse that has a second orientation or shape with respect to positive and negative pressure that is opposite (e.g., mirror image) of the shape/orientation of the first pulse. Although the first and second pulses have a pulse duration of about 1 μs and are about 2 μs apart in FIG. 4C, the pulse interval is not drawn to scale. Other durations and intervals may be used in other implementations, such as those described with reference to FIG. 4A.

FIG. 4D illustrates a Chirp-coded excitation pulse imaging scheme. As illustrated in FIG. 4D, the Chirp-coded excitation pulse imaging scheme has a pulse duration of 3 μs. In other implementations, different pulse durations may be used, such as 2.5 μs, 3 μs, etc. Although, the image pulses have a pressure of 1 to −1 MPa in FIGS. 4B-4D, in other implementations, the image pulses may have different pressures, such as those pressures described with reference to FIG. 4A.

The image pulsing schemes of FIGS. 4B-4D cause an increase in a degree of nonlinear bubble oscillations as compared to conventional therapy systems without imaging or as compared to conventional therapy systems with non-plane wave imaging methods (e.g., non-plane wave B-mode waves). The increased degree of nonlinear bubble oscillations will also increase bubble modulation, and thus will improve the ability of plane wave imaging to increase bubble cloud dissolution. Additionally, the image pulsing schemes of FIGS. 4C and 4D may cause an increase in a degree of nonlinear bubble oscillations as compared to the image pulsing scheme of FIG. 4B. The increased degree of nonlinear bubble oscillations will also increase bubble modulation, and thus will improve the ability of plane wave imaging to increase bubble cloud dissolution. However, the image pulsing scheme of FIG. 4B may be easier to generate and the hardware to generate such pulses may have reduced costs.

Figure 5:
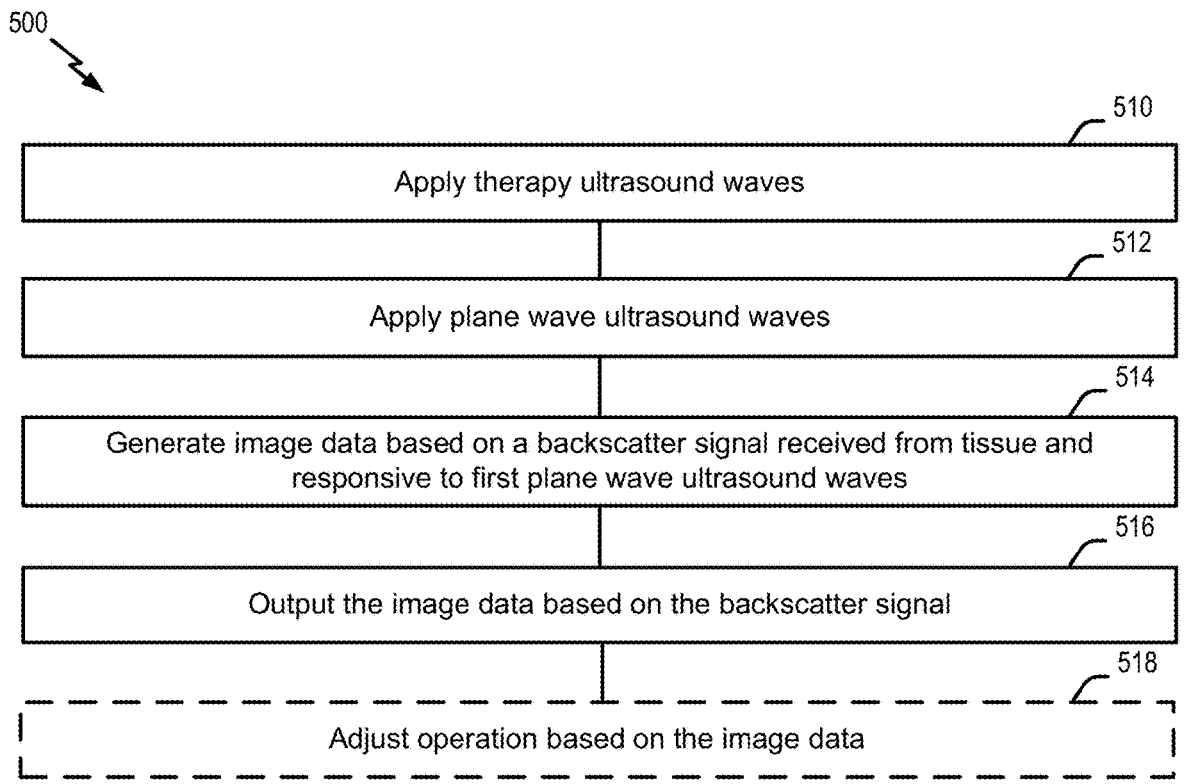
FIG. 5 is a flowchart illustrating an example of a method of operation of a therapy system.

Referring to FIGS. 5-8, flowcharts of examples of operation of a therapy system (and components thereof) are shown. FIG. 5 illustrates a method 500 of providing ultrasound therapy. The method 500 may be performed at or by system 100 (e.g., controller 110, transducer 112, and/or imaging device 114) or system 400 (e.g., one or more components thereof).

Method 500 includes applying therapy ultrasound waves, at 510. For example, the therapy ultrasound waves may include or correspond to therapy ultrasound waves emitted by transducer 112 or transducer 422. To illustrate, transducer 112 emits first therapy ultrasound waves at a first time towards a therapy site (e.g., tissue 118). The first therapy ultrasound waves may include or correspond to a first pulse or therapy pulse.

Method 500 also includes applying plane wave ultrasound waves, at 512. For example, the plane wave ultrasound waves may include or correspond to plane wave ultrasound waves emitted by the imaging device 114 or the imaging array 432. To illustrate, the imaging device 114 emits first plane wave ultrasound waves at a second time, after the first time, towards the therapy site. The first plane wave ultrasound waves may include or correspond to one or more pulses or imaging/modulation pulses.

Method 500 includes generating image data based on a backscatter signal received from tissue and responsive to plane wave ultrasound waves, at 514. For example, the image data may include or correspond to data 194, and may be raw image data, grayscale image data, or binarized (e.g., black and white) image data. The image data may depict a bubble cloud within tissue 118, and may correspond to B-mode image data (e.g., is brightness modulated). To illustrate, tissue 118 produces a backscatter signal by reflecting the first plane wave ultrasound waves. The imaging device 114 or the imaging array 432 receives the backscatter signal and generates image data based on the backscatter signal, such as an intensity thereof. The backscatter signal may include or correspond to one or more signals or pulses, such as a plurality of backscatter signal pulses. Each backscatter signal pulse may correspond to a frame (i.e., image frame) of image data.

Method 500 further includes outputting the image data based on the backscatter signal, at 516. For example, the controller 110 may provide a grayscale image or binarized image on monitor 126 or output the image data to another device for use in analyzing therapy (e.g., for calculating bubble deletion rates).

Additionally, or alternatively (with respect to outputting the image data), method 500 further comprises adjusting operation based on the image data, at 518. For example, the controller 110 or the controller 434 may adjust imaging parameters. As another example, the controller 110 or 410 may adjust therapy parameters. A controller may adjust a parameter by sending an adjustment signal 196 to the ultrasound imaging device 114 or the transducer 112 or adjusting/generating an adjusted excitation signal that drives the imaging device 114 or the transducer 112. Examples of adjustments are described with reference to FIG. 6.

Figure 6:
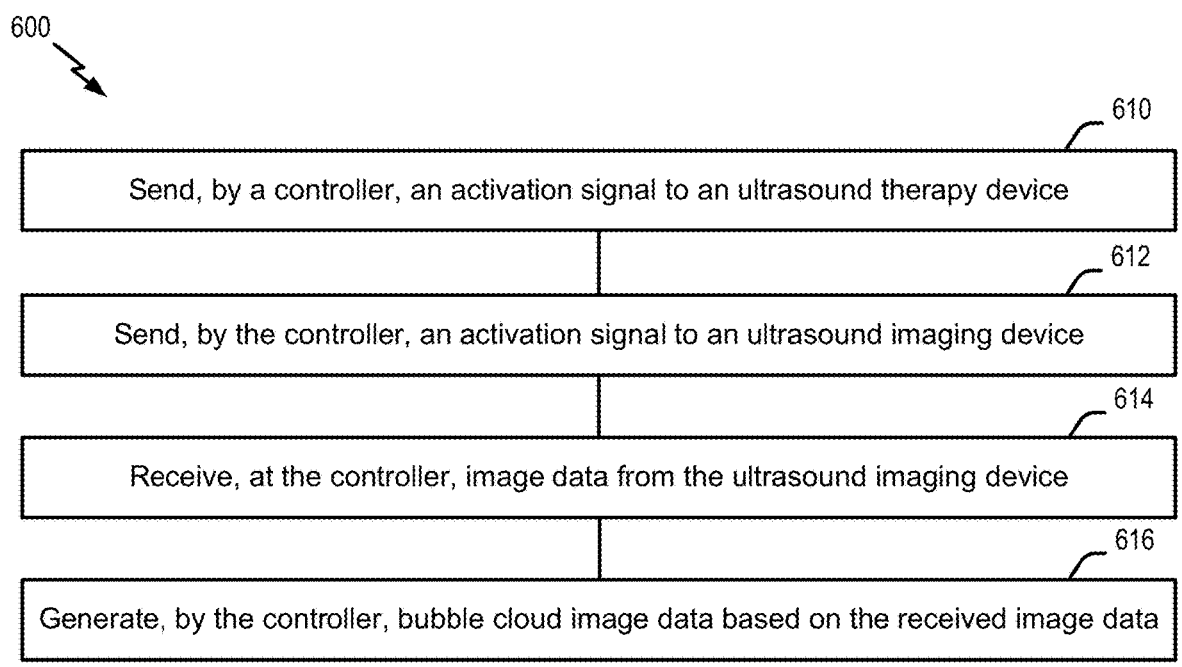
FIG. 6 is a flowchart illustrating an example of a method of operation of a controller of the therapy system.

FIG. 6 illustrates a method 600 of operating (e.g., controlling) a therapy system. The method 600 may be performed at or by system 100 (e.g., controller 110) or the system 400 (e.g., controller 410 and/or controller 434).

Method 600 includes sending, by a controller, an activation signal to an ultrasound therapy device, at 610. For example, the activation signal may include or correspond to the activation signal 192, and the ultrasound therapy device may include or correspond to the transducer 112, the therapy device 412, or the transducer 422. To illustrate, controller 110 sends an activation signal 192 to the transducer 112.

Method 600 also includes sending, by the controller, an activation signal to an ultrasound imaging device, at 612. For example, the activation signal may include or correspond to the activation signal 192, and the ultrasound imaging device may include or correspond to the imaging device 114, the imaging device 414, or the imaging array 432. To illustrate, controller 110 sends a second activation signal 192 to the imaging device 114.

Method 600 includes receiving, at the controller, image data from the ultrasound imaging device, at 614. For example, the image data may include or correspond to data 194, and may be raw image data, grayscale image data, or binarized (e.g., black and white) image data. The image data may depict a bubble cloud within tissue 118, and may correspond to B-mode image data (e.g., is brightness modulated). To illustrate, tissue 118 produces a backscatter signal by reflecting the plane wave ultrasound waves (e.g., a pulse thereof) emitted by ultrasound imaging device. The ultrasound imaging device (e.g., the imaging device 114, the imaging device 414, or the imaging array 432) receives the backscatter signal and generates the image data based on the backscatter signal, such as an intensity thereof.

Method 600 further includes generating, by the controller, bubble cloud image data based on the received image data, at 616. For example, the controller 110 may generate a grayscale image or binarized image based on raw image data or may generate binarized image based on received grayscale image data. As another example, the controller 110 may generate normalized image data based on the received image data.

In some implementations, method 600 further comprises adjusting operation based on the received image data, at 618. For example, the controller 110 or the controller 434 may adjust imaging parameters. As another example, the controller 110 or 410 may adjust therapy parameters. A controller may adjust a parameter by sending an adjustment signal 196 to the ultrasound imaging device 114 or the transducer 112 or adjusting/generating an adjusted excitation signal that drives the imaging device 114 or the transducer 112.

As an illustrative, non-limiting example, the received image data (e.g., two frames thereof or first image data and second image data) can be used to determine a bubble deletion rate. If the bubble deletion rate is above a threshold (e.g., a bubble deletion rate threshold of thresholds 146), the plane wave ultrasound waves are adjusted. In a particular implementation, the plane wave ultrasound waves are reduced in pulse length, frequency, and/or intensity when the bubble deletion rate is above a first threshold, and the plane wave ultrasound waves are increased in pulse length, frequency, and/or intensity when the bubble deletion rate is below a second threshold. The first threshold is greater than the second threshold and the first and second threshold define a range of bubble deletion rates for a particular therapy type, such as prostate tissue therapy.

As another illustrative, non-limiting example, the received image data can be used to determine a bubble cloud size and/or bubble size. If the bubble cloud size and/or bubble size is above a corresponding threshold (e.g., a bubble cloud size and/or bubble size threshold of thresholds 146), the therapy ultrasound waves are adjusted. In a particular implementation, the therapy ultrasound waves are increased in pulse length, frequency, and/or intensity when the bubble cloud size and/or bubble size is above one or more first corresponding thresholds, and the therapy wave ultrasound waves are reduced in pulse length, frequency, and/or intensity when the bubble cloud size and/or bubble size is below one or more second corresponding thresholds. The first thresholds may be greater than the second thresholds and the first and second thresholds may define a range of bubble cloud size and/or bubble size for a particular therapy type, such as prostate tissue therapy.

Figure 7:
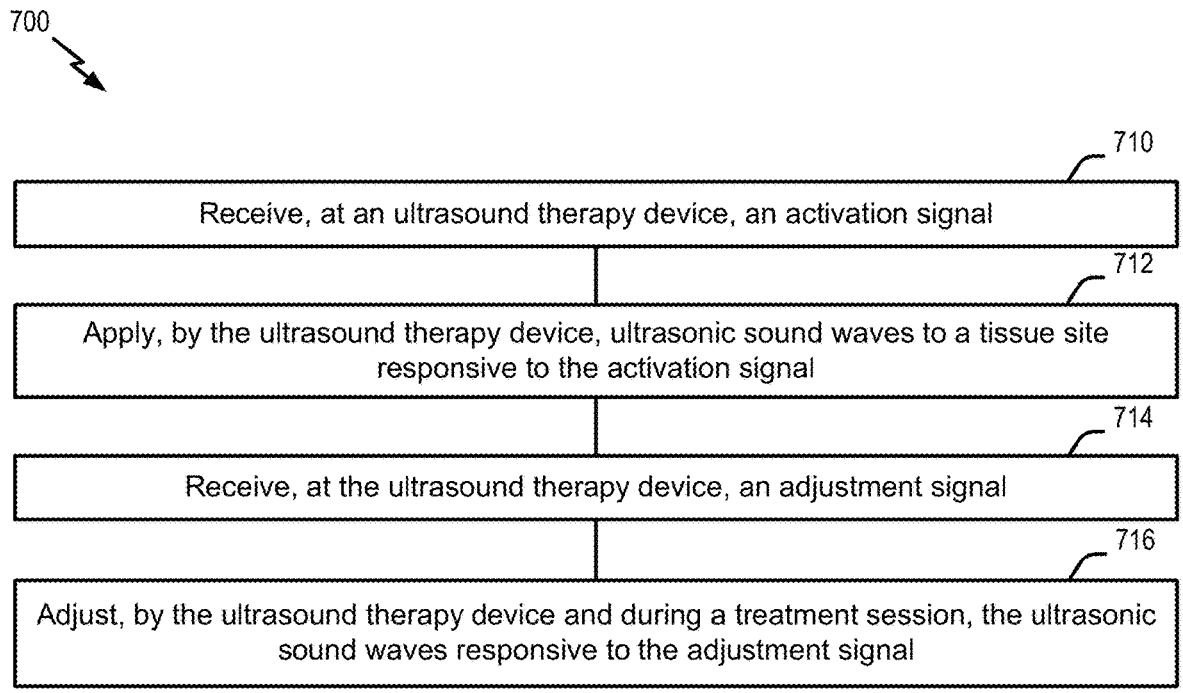
FIG. 7 is a flowchart illustrating an example of another method of operation of a therapy device of the therapy system.

FIG. 7 illustrates a method 700 of manufacturing a compound film. The method 700 may be performed at or by system 100 (e.g., the transducer 112) or the system 400 (e.g., the therapy device 412 and/or the transducer 422).

Method 700 includes receiving, at an ultrasound therapy device, an activation signal, at 710. For example, the activation signal may include or correspond to the activation signal 192, and the ultrasound therapy device may include or correspond to the transducer 112, the therapy device 412, or the transducer 422. To illustrate, the transducer 112 receives an activation signal 192 from the controller 110.

Method 700 also includes applying, by the ultrasound therapy device, ultrasonic sound waves to a tissue site responsive to the activation signal, at 712. For example, the ultrasonic sound waves may include or correspond to therapy ultrasound waves emitted by transducer 112 or transducer 422. To illustrate, transducer 112 emits first therapy ultrasound waves at a first time towards a therapy site (e.g., tissue 118). The first therapy ultrasound waves may include or correspond to a first pulse or therapy pulse. In some implementations, the ultrasound therapy device applies additional therapy ultrasound waves, such as second therapy ultrasound waves or a second pulse, responsive to the activation signal or additional activation signals. Such additional pulses may be interleaved with imaging/modulation pulses.

Method 700 includes receiving, at the ultrasound therapy device, an adjustment signal, at 714. For example, the adjustment signal may include or correspond to an adjustment signal 196. To illustrate, the controller 110 or 410 may adjust one or more therapy parameters of the ultrasound therapy device during a treatment session and the ultrasound therapy device may receive an adjustment signal 196 including an adjusted therapy parameter. As another example, the adjustment signal 196 is an excitation signal and the controller 110 or 410 adjust therapy parameters by adjusting the excitation signal.

Method 700 further includes adjusting, by the ultrasound therapy device and during a treatment session, the ultrasonic sound waves responsive to the adjustment signal, at 716. For example, the controller 110 or 410 may cause adjustment to one or more therapy parameters of the ultrasound therapy device during a treatment session. A therapy parameter of the ultrasound therapy device may be adjusted by receiving an adjustment signal 196 at the transducer 112 or receiving/generating an adjusted excitation signal that drives the transducer 112. To illustrate, the transducer 112 applies second therapy ultrasound waves that are different from the (first) therapy ultrasound waves. The second therapy ultrasound waves are generated based on a second excitation signal that is different from a first excitation signal used to generate the (first) therapy ultrasound waves. The adjustment or adjustment signal 196 may be determined based on plane wave B-mode ultrasound data, as described herein.

Figure 8:
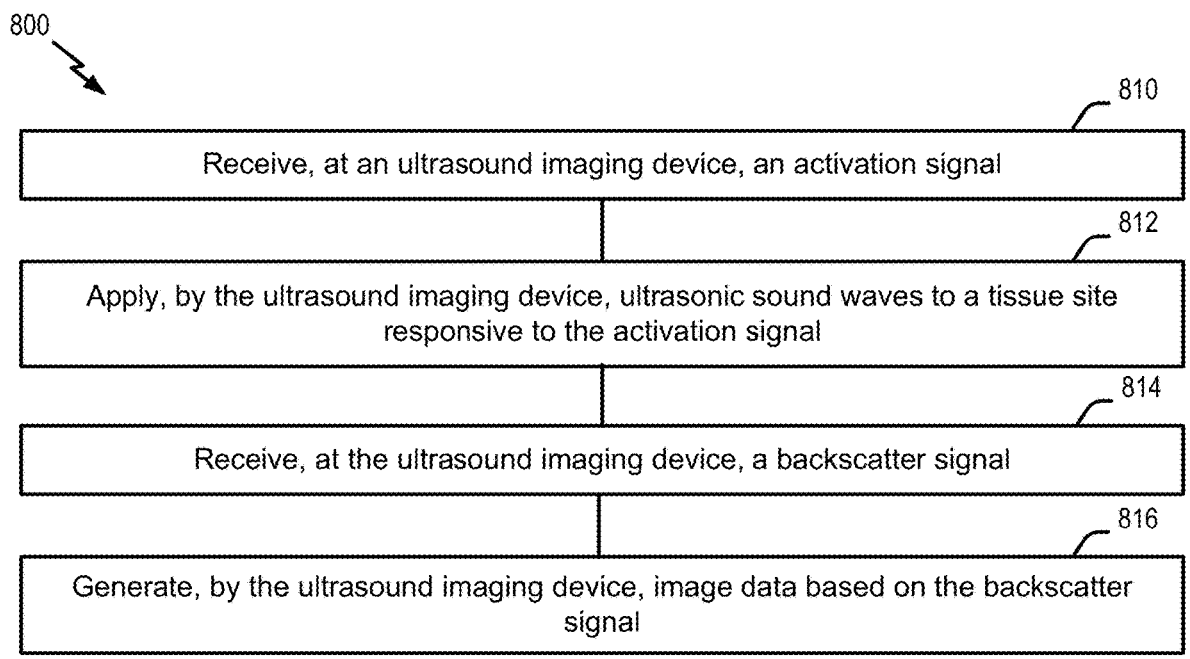
FIG. 8 is a flowchart illustrating an example of a method of operation of an imaging device of the therapy system.

FIG. 8 illustrates a method 800 of manufacturing a compound film. The method 800 may be performed at or by system 100 (e.g., the imaging device 114) or the system 400 (e.g., the imaging device 414, the imaging array 432, and/or the controller 434).

Method 800 includes receiving, at an ultrasound imaging device, an activation signal, at 810. For example, the activation signal may include or correspond to the activation signal 192, and the ultrasound imaging device may include or correspond to the imaging device 114, the imaging device 414, the imaging array 432, or the controller 434. To illustrate, controller 110 sends activation signal 192 to the imaging device 114.

Method 800 also includes applying, by the ultrasound imaging device, ultrasonic sound waves to a tissue site responsive to the activation signal, at 812. For example, the ultrasonic sound waves may include or correspond to plane wave ultrasound waves emitted by the imaging device 114 or the imaging array 432. To illustrate, the imaging device 114 emits first plane wave ultrasound waves at a second time towards the therapy site after therapy ultrasound waves were applied to therapy site at a first time.

Method 800 includes receiving, at the ultrasound imaging device, a backscatter signal, at 814. For example, the backscatter signal may include or correspond to a response signal of the plane wave ultrasound waves or signals (e.g., a pulse thereof). To illustrate, tissue 118 produces a backscatter signal by reflecting the plane wave ultrasound waves emitted by the ultrasound imaging device. The imaging device 114 or the imaging array 432 receives the backscatter signal and/or detects the backscatter signal, such as an intensity thereof.

Method 800 further includes generating, by the ultrasound imaging device, image data based on the backscatter signal, at 816. For example, the image data may include or correspond to data 194, and may be raw image data, grayscale image data, or binarized (e.g., black and white) image data. The image data may depict a bubble cloud within tissue 118, and may correspond to B-mode image data (e.g., is brightness modulated).

Method 800 optionally includes adjusting, by the ultrasound imaging device and during a treatment session, the plane wave ultrasound waves responsive to receiving an adjustment signal, at 716. For example, the controller 110 or the controller 434 may adjust imaging parameters based on an adjustment signal 196. A imaging parameter of the ultrasound imaging device may be adjusted by receiving an adjustment signal 196 at the controller 434 or receiving/generating, at the controller 434, an adjusted excitation signal that drives the imaging array 432. To illustrate, imaging array 432 applies second plane wave ultrasound waves that are different from the (first) plane wave ultrasound waves. The second plane wave ultrasound waves are generated based on a second excitation signal that is different from a first excitation signal used to generate the (first) plane wave ultrasound waves. The adjustment or adjustment signal 196 may be determined based on the received image data. For example, the received image data can be used to determine a bubble deletion rate. If the bubble deletion rate is above a threshold (e.g., a bubble deletion rate threshold of thresholds 146), the plane wave ultrasound waves are adjusted. As an exemplary non-limiting example, the plane wave ultrasound waves are reduced in frequency and/or intensity when the bubble deletion rate is above the threshold.

Thus, method 500 describes method of providing therapy, such as operating a therapy system, method 600 describes method of operating (e.g., controlling) a therapy system, method 700 describes method of providing therapy or controlling a therapy device, and method 800 describes a method of providing ultrasound imaging and bubble modulation during therapy or controlling an ultrasound imaging device. Methods 500-800, individually and in combination, enable ultrasound diagnostic imaging during a treatment bubble modulation with the ultrasound waves/signals/pulses, used for the ultrasound diagnostic imaging. Additionally, such real-time or in treatment feedback enables adjustment of the treatment or imaging during a session such that tissue ablation can be improved or optimized. Accordingly treatment efficacy and patient outcomes are further increased over conventional methods which are not capable of modulating bubbles (in or outside of tissue) and providing real time in treatment feedback.

Figure 20:
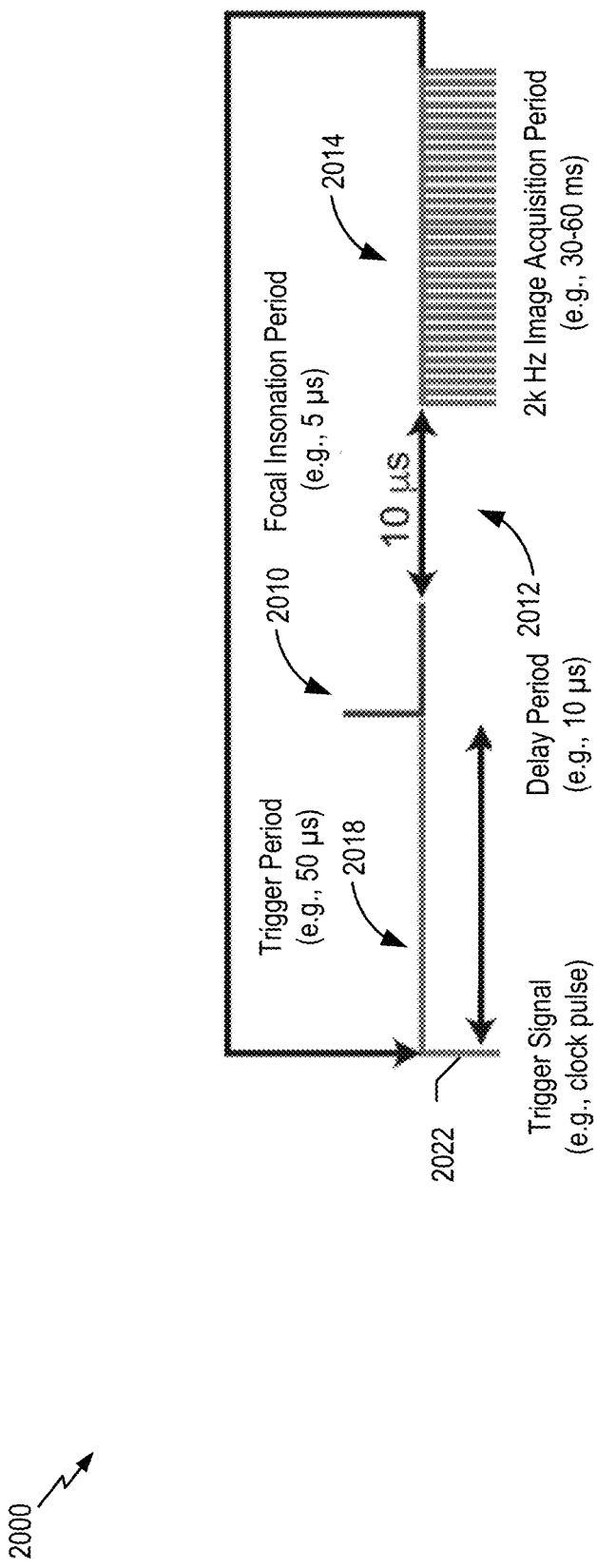
FIG. 20 is a timing diagram of another example of operation of a therapy system.
Figure 21:
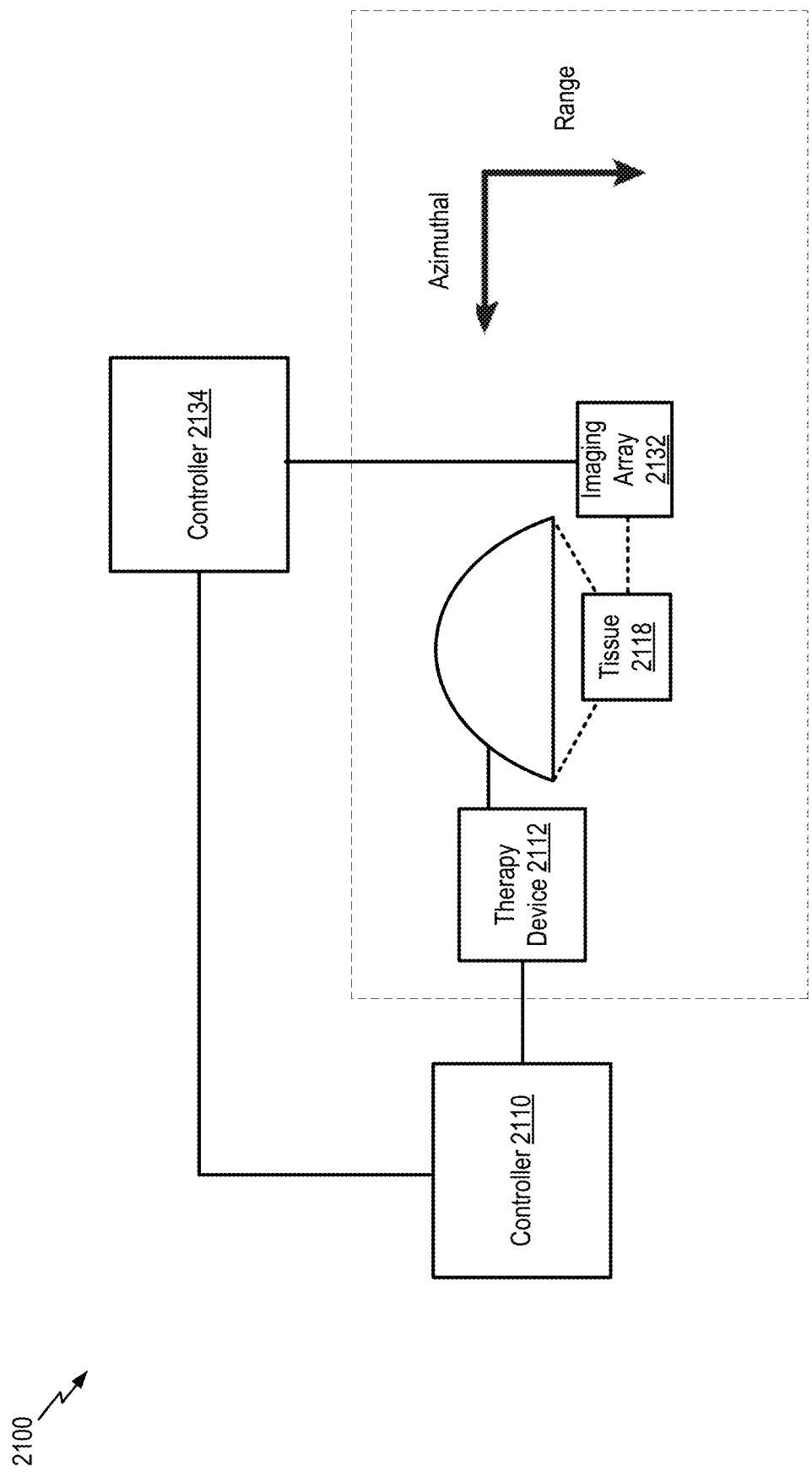
FIG. 21 is a side view of another example of a therapy system.

Referring to FIG. 20, a timing diagram 2000 of another example operation of a therapy system, such as system 100, 400, 2100 of FIG. 21, is illustrated. As illustrated in FIG. 20, timing diagram 2000 illustrates a focal insonation period 2010, a delay period 2012, and a plane wave acquisition period 2014, which together form a treatment cycle. The treatment cycle may be repeated numerous times to form a therapy session.

In some implementations, the periods 2010-2018 are initiated or triggered by a trigger signal 2022. As an illustrative example, the trigger signal 2022 includes or corresponds to the activation signal 192. In other implementations, each of the periods 2010-2018 are initiated or triggered by a corresponding activation signal (i.e., multiple activations are used to control timing).

The focal insonation period 2010 includes or corresponds to a time period or duration where histotripsy therapy or ultrasound therapy is applied to tissue, e.g., tissue 118. As explained above, application of histotripsy therapy or ultrasound therapy may cause bubbles to form in tissue 118 and may cause the bubbles to ablate a portion of tissue 118. The portion of tissue 118 ablated may include or correspond to cells near a focal or focus region of application of ultrasound signals. In some implementations, the focal insonation period 2010 includes a single pulse of ultrasound therapy.

A pulse (or pulses) of the focal insonation period 2010 may have a pulse length (duration) between 3-40 μs in some implementations. In a particular implementation, a pulse of the focal insonation period 2010 has a pulse length of 5-20 μs. Exemplary pulse lengths include pulse lengths of 5 μs, 10 μs, and 20 μs. Therapy ultrasound waves of a pulse (or pulses) of the focal insonation period 2010 may have a frequency (e.g., fundamental frequency) of 800 kHz to 1200 kHz in some implementations. In a particular implementation, therapy ultrasound waves of a pulse of the focal insonation period 2010 have a fundamental frequency of 1 MHz and may be applied at a rate of 10 Hz with pulses of 5 μs duration and 25 MPa peak negative pressure.

Additionally, or alternatively, pulses of the focal insonation period 2010 may have a pulse repetition frequency of 10 to 30 Hertz. In a particular implementation, the pulses of the focal insonation period 2010 have a pulse repetition frequency of about 20 Hertz, i.e., 20 times or pulses a second. Tissue exposure times are based on pulse length and pulse repetition frequency, and exemplary tissue exposure time include 10, 20, and 40 ms. In some implementations, tissue exposure times may be 5 ms to 60 ms.

In some implementations, a peak negative pressure of a pulse of the focal insonation period 2010 is between 10 to 30 MPa. In particular implementations, the peak negative pressure is between 15-25 MPa or is greater than 15 MPa. One exemplary peak negative pressures is 25 MPa.

In some implementations, a derated focal peak negative pressure of a pulse of the focal insonation period 2010 is between 10-30 MPa. In particular implementations, the derated focal peak negative pressure is between 12-23 MPa or is greater than 12 MPa. Exemplary derated focal peak negative pressures include 12, 18, and 23 MPa.

In some implementations, a derated peak positive pressure of pulses of the focal insonation period 2010 are between 50-150 MPa. In particular implementations, the derated peak positive pressure is between 77-105 MPa or is greater than 77 MPa. Exemplary derated peak positive pressures include 77, 105, 123 MPa.

The delay period 2012 includes or corresponds to a time period or duration where no ultrasound is being direction at the tissue. Such a time period may enable improved imaging and reduced constructive interference between therapy ultrasound signals and imaging/bubble modulation ultrasound signals.

The image wave acquisition period 2014 include or corresponds to a time period or duration where plane wave ultrasound signals are applied to tissue, e.g., tissue 118, where backscatter signals generated therefrom are processed, or both. For example, the bubble clouds may be monitored with either standard plane wave, pulse inversion plane waves, or chirp-coded excitation schemes, such as described with reference to FIGS. 4A-4C. Pulse inversion plane waves and chirp-coded excitation schemes may correspond to bubble specific sequences. To illustrate, such schemes may perform better for particular type of bubbles, such as bubbles or bubble clouds with particular dimensions.

For the plane wave and pulse inversion acquisitions, the imaging pulse may have a fundamental frequency of approximately 4 to 6 MHz and may have a pulse duration of approximately 0.1 to 0.3 μs. As an illustrative example, the fundamental frequency is 5 MHz and the pulse duration is 0.2 μs.

For chirp-coded excitation imaging, the pulse bandwidth may be in the range of approximately 4 to 7 MHz over a duration of approximately 1 to 3 μs. As an illustrative example, the pulse bandwidth is between 4.8 to 6 MHz over a duration of 2 μs.

For all sequences, the electrical excitation to the imaging array may be 5V or 25 V. In some implementations, the image wave acquisition period 2014 has a duration of 30-60 ms, such as 45 ms.

In some implementations, plane wave ultrasound signals may be applied to tissue, such as for bubble cloud control or modulation, longer than or without processing the backscatter signals. As an illustrative example, plane wave ultrasound signals may be sent during the entire image acquisition period 2014 and images are only captured during a portion of image acquisition period 2014, such as a second half. As an additional example, the delay period 2012 may be reduced or eliminated to add additional plane wave ultrasound to control bubble modulation. In some implementations, the image acquisition period 2014 includes a multiple pulses and multiple corresponding backscatter signals. Thus, in such implementations, multiple images (e.g., image frames) are captured during a single image acquisition period 2014.

In some implementations, a peak negative pressure of pulses of the image acquisition period 2014 are between 10 kPA to 10 MPa. In particular implementations, the peak negative pressure is between 420 kPA to 6.7 MPa or is greater than 420 kPA.

Additionally, or alternatively, ultrasound waves of pulses of the image acquisition period 2014 may have a frequency (e.g., fundamental frequency) of 800 kHz-10 MHz. In a particular implementation, ultrasound waves of the pulses of the image acquisition period 2014 have a frequency of about 6.25 MHz. In another particular implementation, ultrasound waves of the pulses of the image acquisition period 2014 have a frequency of about 1 MHz.

In a particular implementation (e.g., plane wave or pulse inversion implementations), pulses of the image acquisition period 2014 may have a 5 MHz fundamental frequency and a 0.3 μs pulse duration. In another particular implementation (e.g., chirp-coded excitation imaging implementations), a pulse bandwidth of the pulses of the image acquisition period 2014 may be 4.8 to 6 MHz over a 2 μs duration.

In a particular implementation, the delay period 2012 is about 50 μs and an imaging device (e.g., 114) starts capturing images about 50 μs after the focal insonation period 2010. Additional, plane wave types and plane wave acquisition periods may be used in other implementations, as described with reference to FIG. 3.

This timing sequence illustrated in FIG. 20 may repeat for many cycles to form a therapy cycle or treatment session. For example, one therapy cycle or treatment session may include 2000 cycles depicted in FIG. 20. The process may be adjusted mid cycle or from cycle to cycle. For example, the timing of the signals may be adjusted by adjusting the trigger signal 2022. As another example, image data may only be generated once every "N" number cycles. For example, backscatter signals are generated each plane wave acquisition period from the emitted ultrasound, but the backscatter signals are only received and/or processed once every 10 cycles, 200 cycles, etc., to form image data, bubble deletion rates, adjustments, or a combination thereof.

In a particular implementation, there is a delay between the trigger signal 2022 an activation of focal insonation, i.e., start of period 2018. The delay may be used to prevent constructive interference between imaging waves of a previous cycle and therapy waves of a next or current cycle or may represent the time it takes for signal propagation and processing by components.

The timing sequences illustrated in FIG. 20 enables ultrasound diagnostic imaging during a treatment session. Additionally, the timing sequences enable bubble modulation with the ultrasound waves/signals/pulses, used for the ultrasound diagnostic imaging. Accordingly, a therapy system, such as system 100, 400, or 2100, includes benefits and advantages over conventional therapy systems because such a therapy system can modulate bubble clouds within tissue and can image bubble clouds in tissue in real-time (i.e., during treatment). Therefore, treatment efficacy and patient outcomes are increased.

Additionally, such real-time or in treatment feedback enables adjustment of the treatment or imaging during a session such that tissue ablation can be improved or optimized. Accordingly, treatment efficacy and patient outcomes are further increased over conventional methods which are not capable of modulating bubbles (in or outside of tissue) and providing real time in treatment feedback.

Referring to FIG. 21, a top view of an example of therapy system 2100 is illustrated. System 2100 includes a controller 2110, a therapy device 2112, and an imaging device 2114. System 2100 may include or correspond to therapy system 100, and operate with timings described in FIGS. 2, 3, and 20. The therapy device 2112 includes a histotripsy transducer 2122 (also referred to as "transducer 2122") and the imaging device 2114 includes an imaging array 2132 and a controller 2134. The therapy device 2112 and/or the histotripsy transducer 2122 may include or correspond to the transducer 112 of FIG. 1. As illustrated in the example of FIG. 21, the transducer 2122 is controlled by the controller 2110, i.e., receives an excitation signal from the controller 2110 which drives the transducer 2122 to generate the therapy ultrasound signal/pulse. The therapy pulse generates or causes a bubble cloud within tissue 2118. As multiple therapy pulses are applied, the bubble cloud grows in the azimuthal axis 2154 and into a nearfield (leftward in FIG. 21) relative to a focus of the transducer 2122.

The imaging array 2132 is configured to capture image data. In some implementations, the imaging array 2132 is configured to capture backscatter signal intensity data. In some implementations, the imaging array 2132 is a linear array. As illustrated in the example of FIG. 21, the imaging array has a focus area width of 3 centimeters. In other implementations, the focus area and/or the width thereof of the imaging array 2132 may be larger or smaller based on a size of a therapy site and the transducer 2122.

The imaging array 2132 may also be configured to generate and emit an image pulse signal, which is partially reflected by tissue 2118 to create the backscatter signal. As an illustrative, non-limiting example, the imaging array 2132 is configured to generate a 5 MHz imaging pulse.

The controller 2134 is configured to control or "drive" the imaging array 2132. In some implementations, the controller 2134 is configured to process or partially process the image data. In other implementations, the controller 2134 sends the image data (e.g., raw image data or intensity values) to the controller 2110. The controller 2134 may include components similar to controller 110. For example, the controller 2134 generated and sends electrical excitation signals to the imaging array 2132 of either 5 V or 25 V.

As illustrated in FIG. 21, the imaging array 2132 of the imaging device 2114 is oriented to monitor bubble cloud activity along a central axis (e.g., an azimuth/range plane of the imaging array as illustrated in FIG. 21) of the histotripsy transducer 2122. The histotripsy transducer 2122 may have a 7.5 cm focal length and 10 cm outer diameter. The histotripsy transducer 2122 may be placed into the tissue 2118, adjacent to the 2118, or oriented at the tissue 2118. As illustrated in FIG. 21, the histotripsy transducer 2122 is positioned (i.e., located and oriented) such that a focus of the histotripsy transducer 2122 is at a depth of 2 cm, 2162, into the tissue in the azimuthal axis 2154. A distance 2164 between the imaging array 2132 and the focus of the histotripsy transducer 2122 is 3 cm in the range axis 2152. The histotripsy transducer 2122 and the imaging array 2132 may be aligned confocally, as described with reference to FIG. 2, and may be positioned in a similar manner to the histotripsy transducer 222 and the imaging array 232 of FIG. 2. In some implementations, system 2100 includes a three-axis positioning device or system, such as three axis positioning device 442 of FIG. 4A.

In some implementations, the system 2100 includes multiple imaging arrays. For example, each imaging array acquires image data in a fixed two-dimensional plane. Thus, to capture a larger portion of the volume of the bubble cloud, multiple imaging arrays may be positioned in parallel or angled from one another such that additional image "slices" of the bubble cloud are captured.

It is noted that one or more operations described with reference to one of the methods of FIGS. 5-8 may be combined with one or more operations of another of FIGS. 5-8. For example, one or more operations of method 600 may be combined with one or more operations of method 700. Additionally, or alternatively, one or more operations described above with reference to FIGS. 1-4A may be combined with one or more operations of FIG. 5, FIG. 6, FIG. 7, FIG. 8, or a combination of FIGS. 5-8.

Experimental Results

Experiments were conducted on tissue mimicking phantoms subjected to therapeutic ultrasound to determine bubble cloud behavior in the presence of plane wave ultrasound and if plane wave ultrasound could be used to image bubble clouds. The objective of the experiment was to monitor translation of histotripsy-induced bubble clouds and to monitor changes in area and grayscale of histotripsy-induced bubble clouds in the tissue mimicking phantoms (e.g., a prostate tissue phantom). The potential to modulate the bubble cloud behavior with high acoustic output from the plane wave imaging sequence was also explored. To predict the bubble cloud behavior, an analytic model based on histotripsy-induced bubble expansion (Bader and Holland 2016) and a zero-order diffusion equation (Eller 1965) was developed to compute the time for bubble dissolution. Predictions from the analytic model were compared to numerical computations from previous studies (Bader and Bollen 2018) and experimental observations.

I. Methods

A. Tissue Phantom Production

Tissue phantoms (also referred to herein as phantoms) were manufactured utilizing an established protocol disclosed in (Bader et al. 2016a, 2018a). The phantoms included agarose (3.7 g), deionized water (147.2 mL), n-propanol (12.8 mL), and evaporated milk (240 mL). Commercially available evaporated milk was gently stirred on a hot plate to reach a final temperature of about 55° C. Agarose powder (A9539 Sigma-Aldrich Co. St. Louis, MO, USA) was dissolved into a 0.2 µm filtered, deionized water (NANOPure Diamond, Barnstead International, Dubuque, IA, USA) and n-propanol solution by heating in 30 seconds increments in a microwave at 700 W power until clear. The heated agarose/n-propanol solution was placed in a heated (55° C.) ultrasonic cleaning bath for 30 minutes while continuously evacuating at 50 kPa. The degassed agarose/n-propanol solution was combined with the heated evaporated milk, poured into a mold, and allowed to solidify at 5° C. overnight. This formation has previously been shown to replicate the density, sound speed, elastic modulus, and frequency-dependent acoustic attenuation spectra of ex vivo prostate tissue (Bader et al. 2016a). The phantoms employed in this study reproduced the frequency-dependent attenuation of prostate tissue (Bader et al. 2016a), a key parameter of the bubble cloud behavior (Bader et al. 2018a).

The use of a phantom allowed specified, consistent medium properties (Bader et al. 2016a) throughout the experiment. Although this experiment was performed with an in vitro approach, the results can apply to in vivo application. For example, although a population of cavitation nuclei of the phantoms may not replicate a population of cavitation nuclei found in real tissue (which may affect the threshold for individual bubble formation), bubble dynamics initiated by highly shocked histotripsy excitations are largely independent of an initial bubble diameter and viscoelastic properties of the medium (tissue in in vivo applications) (Maxwell et al. 2013, Bader and Holland 2016). Accordingly, such differences in cavitation nuclei populations are not likely to materially affect bubble cloud formation. As another example, lack of "scatterers" (e.g., ingredients which reflect ultrasound waves) used in the phantom minimized the presence of cavitation nuclei as compared to real tissue, but also resulted in a medium that was more hypoechoic (i.e., lower echogenicity (lower ability to "bounce an echo"/produce a backscatter signal) and appears darker in images) than real tissue (Szabo 2004).

B. Histotripsy Insonation

Histotripsy pulses were generated with a 1-MHz ultrasound transducer (transducer) having an 8-element annular array (transducer elements) with a 10-cm aperture and 9-cm focal length from Imasonic, Voray sur l'Ognon, France. The transducer elements were simultaneously driven in parallel by a custom designed and built class D amplifier and matching network described in (Hall and Cain 2006). The transducer was calibrated in water at the focus of the transducer for peak negative pressures up to 18.3 MPa with a fiber optic hydrophone (FOPH 2000, RP Acoustics, e.K., Leutenbach, Germany) (Bader et al. 2016b). Direct calibration of the histotripsy transducer was not possible for greater peak negative pressures due to cavitation, and the peak negative pressure was estimated following the analytical methods provided in Maxwell et al. (2013). A total of 2000 histotripsy pulses of 5, 10, or 20 µs duration were delivered to each phantom at a pulse repetition frequency of 20 Hz (resulting in 10, 20, or 40 ms total histotripsy exposure time, respectively). The focal peak negative pressure of the pulse was 12, 18, or 23 MPa, derated based on the acoustic attenuation coefficient of the phantom assuming a 1-MHz fundamental frequency (0.46 dB/cm) (Bader et al. 2016a). The derated peak positive pressures were estimated following the methods of Canney et al. (Canney et al. 2010) to be 77, 105, and 123 MPa. The largest pressure level, beyond the calibration of the transducer calibration, was estimated based on numerical simulation (Rosnitskiy et al. 2017). The insonation conditions employed in this study span those previously employed for histotripsy (Maxwell et al. 2012, Khokhlova et al. 2015).

C. Experimental Protocol

Phantoms were degassed for two hours in deionized water at a partial pressure of 2 kPa, after which they were affixed to a three-axis positioning system of TDC001, by Thorlabs Inc, Newton, NJ, USA, immersed in a tank of degassed (20% dissolved oxygen), filtered (10-μm pore size) water. Bubble clouds generated by 5-μs histotripsy pulses in the water tank were visualized with plane wave B-mode images acquired with an L11-4v imaging array from Verasonics, Inc., Kirkland, WA, USA which was driven by a research ultrasound scanner Vantage 128 from Verasonics, Inc. The bubble cloud location in the image was denoted as the free field focus of the histotripsy transducer, (Vlaisavljevich et al. 2013b).

Referring to FIG. 9A, a side view of the experimental set up for histotripsy bubble cloud generation in the tissue mimicking phantom is illustrated. The L11-4v imaging array was oriented to monitor bubble cloud activity with high frame rate imaging along a central axis (i.e., azimuth/range plane of the imaging array) of the histotripsy transducer (9-cm focal length, 10-cm outer diameter). The histotripsy transducer and phantom were then positioned such that the histotripsy transducer focus was at a depth of 2 cm into the phantom. The distance between the imaging array and the histotripsy focus was fixed at 3 cm. The output of the imaging array was at this position was calibrated by a needle hydrophone HNP-0400 from Onda Corporation, Sunnyvale, CA, USA.

During operation, a series of histotripsy pulses (e.g., 2000 histotripsy pulses) were applied and the exposure conditions were randomized. During the excitation sequence of 2000 histotripsy pulses, a high frame rate plane wave imaging sequence was triggered by the histotripsy electronics. Referring to FIG. 9B, an exemplary timing diagram for the acquisition of high frame rate plane wave B-mode images following the histotripsy focal insonation is depicted. In FIGS. 9C and 9D, exemplary diagrams illustrating pressure generated by histotripsy pulses over time for the focal insonation period are depicted.

Frames (e.g., ultrasound image data) were acquired from about 147 μs-179 μs to 10 ms after the histotripsy focal insonation at a rate of 11.5 kHz, and from 10 ms to 50 ms at a rate of 1 kHz (142 frames total). Strong hyperechoic interference patterns prevented acquisition of frames prior to 179 μs post focal insonation. The imaging sequence was acquired every 200$^{th}$ histotripsy pulse due to data transfer limitations, and to ensure observation of a new bubble cloud when the imaging sequence was triggered. The peak negative pressure for the plane wave imaging sequence varied between 420 kPa (lowest output for imaging array) and 6.7 MPa (highest output for imaging array).

D. Image Processing

Figures 10A, 10B:
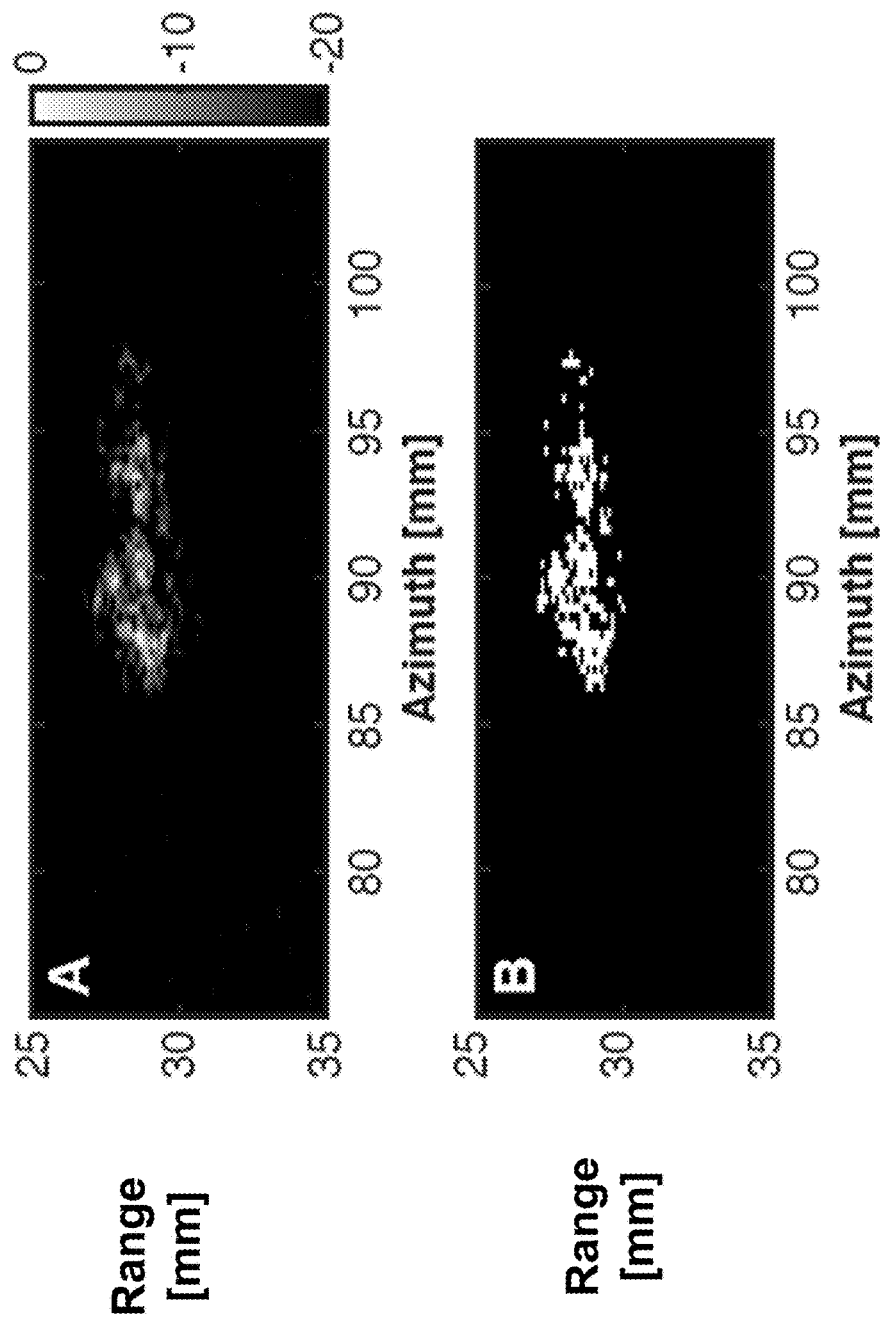
FIG. 10A is an image depicting a plane wave image of a bubble cloud acquired with the setup of FIG. 9A and the plane wave imaging sequence of FIG. 9B.
FIG. 10B is an image depicting a Binarized plane wave image of the image of FIG. 10A.

Plane wave images were downloaded and analyzed offline at the completion of each study. Pixels indicative of bubble cloud were determined by applying Otsu's method to the grayscale image via the 'imbinarize' function in MATLAB, a registered trademark of The Mathworks, Natick, MA, USA, as shown in FIG. 10A. For each frame, the bubble cloud area and mean grayscale values (e.g., intensity values) were recorded. The azimuth position of the bubble cloud, reported in terms of the bubble cloud centroid, was also assessed (Haworth et al. 2015). The range of the histotripsy transducer focus was fixed at 30 mm in the imaging array plane as illustrated in FIG. 9A. Trends in the bubble cloud area, azimuthal position, or grayscale with time were computed using a Pearson correlation coefficient.

Referring to FIGS. 10A and 10B, representative bubble cloud images acquired with the plane wave imaging sequence of FIG. 9B are illustrated. In FIG. 10A, the histotripsy pulse had parameters of a 10 μs pulse duration and an 18 MPa peak negative pressure and is propagating left to right in the image. The pixel values are reported in terms of dB relative to the maximum grayscale value, as indicated in the colorbar of FIG. 10A. FIG. 10B depicts a Binarized plane wave image of the image of FIG. 10A.

E. Computations of Gas Diffusion During Histotripsy Excitation

The time-dependent bubble diameter was computed numerically using a modified version of the Gilmore equation, Equation (1), as described previously in (Church 1989, Bader and Bollen 2018). Briefly, an adaptive fourth-order Runge-Kutta algorithm was implemented in MATLAB to solve the modified version of the Gilmore model, Equation (1):

$$\left(1 - \frac{\dot{R}}{C}\right)R\ddot{R} + \frac{3}{2}\left(1 - \frac{\dot{R}}{3C}\right)\dot{R}^2 = \left(1 + \frac{\dot{R}}{C}\right)H + \frac{\dot{R}}{C}\left(1 - \frac{\dot{R}}{C}\right)R\frac{dH}{dR} \quad (1)$$

where R is the time dependent bubble radius, the diacritic dot denotes the temporal derivative, and C is the sound speed in the medium at the bubble wall. The enthalpy, H, is defined by Equation (2) and in terms of the medium equation of state:

$$H = \int_{P_\infty}^{P(R)} \left(\frac{P' + B}{A}\right)^{1/m} dP' \quad (2)$$

where A, B, and m are defined following Lastman and Wentzell (1981), and $P_\infty$ is the pressure far from the bubble wall. The pressure at the bubble wall, P(R), is defined by Equation (3) and in terms of the surface tension σ, viscosity μ, shear modulus G, gas pressure $P_g$ and initial bubble radius $R_0$:

$$P(R) = P_g - \frac{2\sigma}{R} - \frac{4\mu\dot{R}}{R} - \frac{4G}{3}\left[1 - \left(\frac{R_0}{R}\right)^3\right] \quad (3)$$

Soft tissues are the intended targets for histotripsy ablation. Thus, Equation (3) varies from the equations in Church (1989) through the addition of the last term, which accounts for medium elasticity through the Kelvin-Voigt model. The gas pressure is dependent on the time-varying number of moles of gas in the bubble n, and was computed following the methods of Church (1989).

Analytic estimation of diffusion was computed based on a high-frequency zero-order solution of the diffusion equation (Eller 1965), Equation (4):

$$n = n_0 + 8\sqrt{\pi D t \left\langle\left(\frac{R}{R_0}\right)^4\right\rangle} R_0^2 C_0 \left\{\frac{C_\infty}{C_0} - \frac{\left\langle\left(\frac{R}{R_0}\right)\right\rangle}{\left\langle\left(\frac{R}{R_0}\right)^4\right\rangle}\right\} \quad (4)$$

where $n_0$ is the initial number of moles of gas within the bubble, D is the diffusion constant, t is time, $C_0$ is the saturated gas concentration, and $C_\infty$ is the gas concentration in the medium. For histotripsy-induced bubble expansion, the second term in the curly brackets is on the order of $\sim 10^{12}$, and can be neglected for even well-degassed media.

The angled brackets denote a time-averaged quantity, and can be estimated analytically following Bader and Holland (2016). Bubble growth for a multiple cycle histotripsy pulse is most rapid over the first tensile (Bader and Holland 2016), and the time-dependent bubble radius can be estimated by Equation (5) as:

$$R = R_0 + Vt \quad (5)$$

where the bubble wall velocity V is as described by Apfel (1981). Over the compressional phase of the histotripsy pulse, the time-averaged bubble radius is approximately equal to $R_1$ and the time-averaged quantity in Equation (4) can be approximated in Equation (6) as:

$$\left\langle \left(\frac{R}{R_0}\right)^4 \right\rangle \sim \left(\frac{R_1}{R_0}\right)^4 \left(1 - \frac{f_0}{2f_{\text{eff}}}\right) + \frac{1}{160}\frac{f_0}{f_{\text{eff}}}\left(\frac{V}{R_0 f_{\text{eff}}}\right)^4 \quad (6)$$

where $f_0$ is the fundamental frequency of the histotripsy pulse, and $f_{\text{eff}}$ is the frequency associated with the extended tensile pulse of the shocked histotripsy waveform (see Equation 7 in Bader and Holland (2016)). Beyond the first cycle, the time-dependent bubble radius can be approximated as $$R_1 + \sqrt{\frac{2|\langle p_{AC} \rangle|}{3\rho}} \, t,$$

where $p_{AC}$ is the time-dependent acoustic pressure waveform. The time-averaged bubble radius to the fourth power in Equation (4) can thus be estimated by Equation (7) as:

$$\left\langle \left(\frac{R}{R_0}\right)^4 \right\rangle \sim \left\langle \left(\frac{R}{R_0}\right)^4 \right\rangle_1 / \tau + \frac{f_0}{5\tau R_0^4 dR}\left[\left(R_1 + \frac{dR(\tau-1)}{f_0}\right)^5 - R_1^5\right] \quad (7)$$

where $\tau$ is the number of cycles of the histotripsy pulse, the first term is the time-averaged bubble radius to the fourth power over the first cycle as evaluated by Equation (6), and $$dR = \sqrt{\frac{2|\langle p_{AC}\rangle|}{3\rho}}.$$

Utilizing Equation (6) for a single cycle pulse, or Equation (7) for a multiple cycle pulse, in Equation (4) thus provides an analytic assessment of the gas content of the bubble for histotripsy-induced bubble expansion. Once the number of moles n was computed analytically via Equation (4) or numerically via Equation (1), the molar-dependent equilibrium radius of the bubble, $R_{0n}$, was computed by Equation (8) as:

$$R_{0n} = \left[\frac{3k_B T n}{4\pi \left(P_0 + \frac{2\sigma}{R_0}\right)}\right]^{1/3} \quad (8)$$

where $k_B$ is Boltzmann's constant and T is the medium temperature. The time for passive dissolution of the gas-filled bubble assessed via Equation (8) was computed following Neppiras (1980).

The following values were used for the medium properties: surface tension $\sigma = 0.056$ N/m (Church et al. 2015, Holland and Apfel 1989), dynamic viscosity $\mu = 0.005$ kg/m/s (Church et al. 2015, Holland and Apfel 1989), shear modulus G=44 kPa (Bader et al. 2018a), and temperature T=293 K. The diffusion constant $D = 1.94 \times 10^{-9}$ m²/s was based on the movement of gases in agarose gels from (Muhr and Blanshard 1982), and the saturated gas concentration $C_0 = 0.822$ mol/m³ was based on air dissolved in water. The gas concentration in the medium was set to 60% based on the measured dissolved oxygen concentration of the solidifying agarose/evaporated milk mixture. The diameter of the bubble nucleus, $2R_0$, was set to 20 nm to provide an upper estimate for the maximum diameter of histotripsy-induced cavitation based on (Bader and Holland 2016).

II. Results

A. Bubble Cloud Generation

Figure 11:
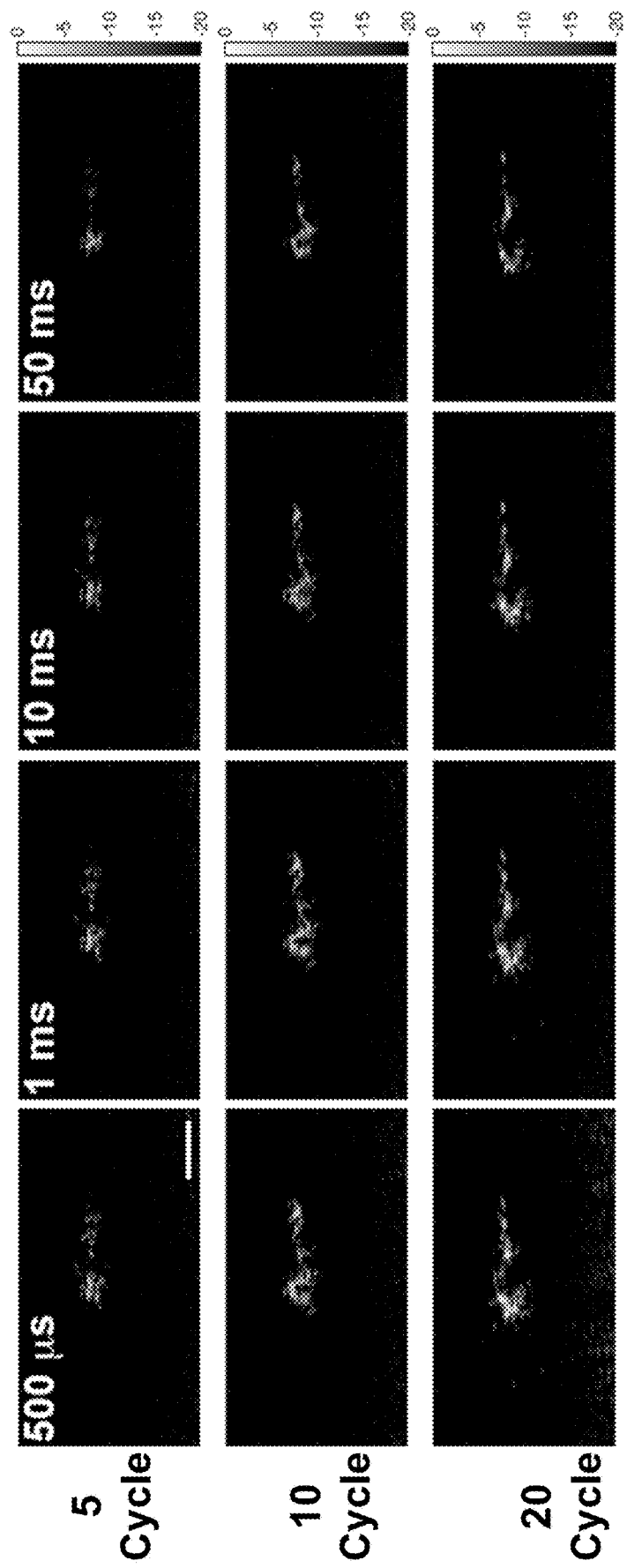
FIG. 11 is a series of images of histotripsy-induced bubble clouds at various times during particular cycles.

For all insonation conditions, bubble clouds were generated within the phantom. Typical observations of the bubble cloud dynamics are displayed in FIG. 11. Referring to FIG. 11, examples of high frame rate plane wave image observations of histotripsy-induced bubble clouds are illustrated. In FIG. 11, a top row depicts a Five-cycle duration histotripsy pulse, a middle row depicts Ten-cycle duration histotripsy pulse, and a bottom row depicts a Twenty-cycle duration histotripsy pulse. The time at which the image was acquired after the conclusion of the histotripsy pulse is noted in the upper right corner (top row only). The grayscale colormap is reported in terms of decibels, normalized to the maximum grayscale of the image acquired at 500 µs for each respective data set (i.e. each respective pulse duration). The histotripsy pulse had a peak negative pressure of 18 MPa (107 MPa peak positive pressure), and was propagating from left to right in each image. The white line in the lower right portion of the image corresponds to 5 mm (top left most panel only). As shown in FIG. 11, the bubble cloud persisted over the entire 50 ms observation period.

Figure 12:
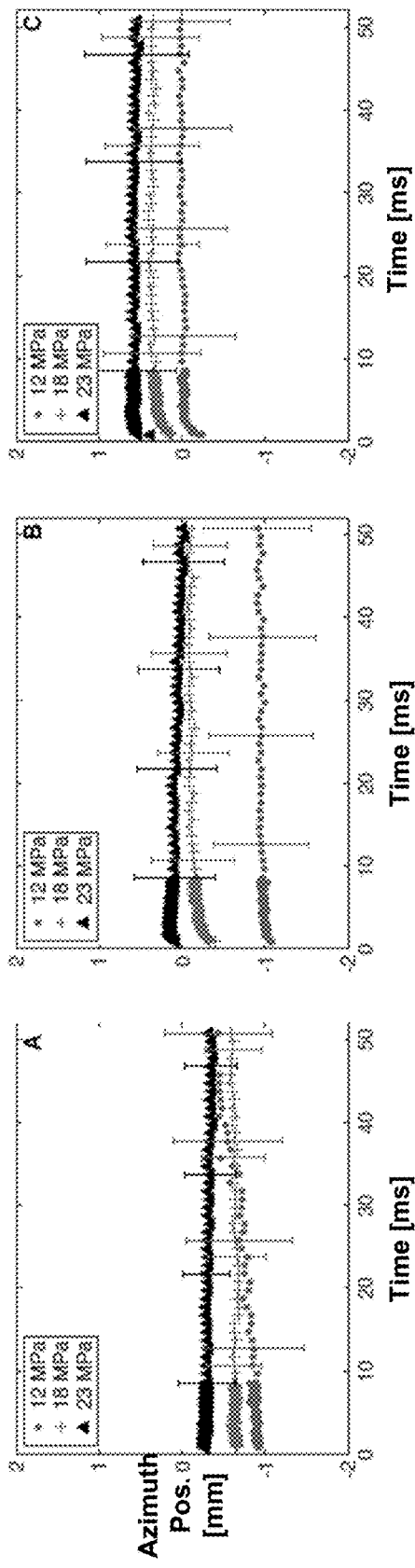
FIG. 12 is a series of diagrams illustrating azimuthal positions of bubble cloud as a function of time for different duration histotripsy pulses.

The azimuthal location of the bubble cloud, noted by the centroid of the bubble cloud grayscale, changed on average for all insonation by 3.8±3.1% (0.18±0.15 mm) over 50 ms, as shown in FIG. 12. Referring to FIG. 12, Azimuthal position of the bubble cloud as a function of time for (A) 5 s, (B) 10 µs, or (C) 20 µs duration histotripsy pulse. The peak negative pressure of the histotripsy pulse is noted in the legend. Error bars are representative of data throughout the duration of image acquisition. Azimuthal positions are relative to the focus of the histotripsy source under linear conditions, with negative values indicating movement towards the transducer.

Figure 13:
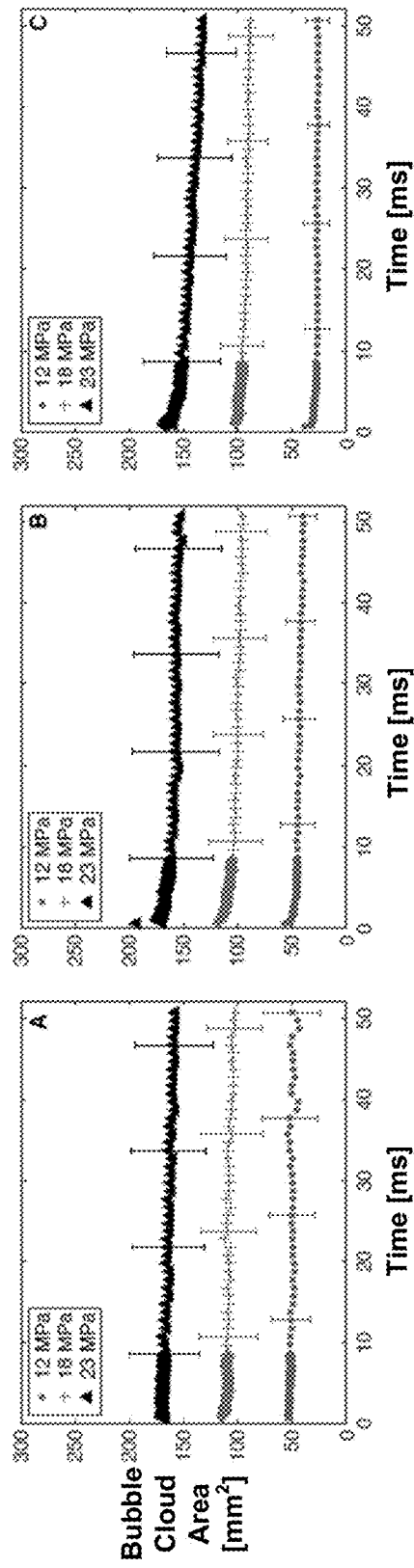
FIG. 13 is a series of diagrams illustrating bubble cloud area as a function of time for different duration histotripsy pulses.

The area of the bubble cloud decreased on average for all insonation conditions by 13.0±7.8% (12.6±10.1 mm²), as illustrated in FIG. 13. Referring to FIG. 13, bubble cloud area as a function of time is depicted for (A) 5 µs, (B) 10 µs, or (C) 20 µs duration histotripsy pulses. The peak negative pressure of the histotripsy pulses is noted in the legend. Error bars are representative of data throughout the duration of image acquisition. The changes in position and area of the bubble cloud were statically significant for most insonation conditions (p<0.05 except bubble cloud area for the 20-µs pulse duration with a 23-MPa peak negative pressure pulse), though the changes in position and area are not substantial over the time scale considered in FIG. 13.

B. Bubble Cloud Grayscale

Figure 14:
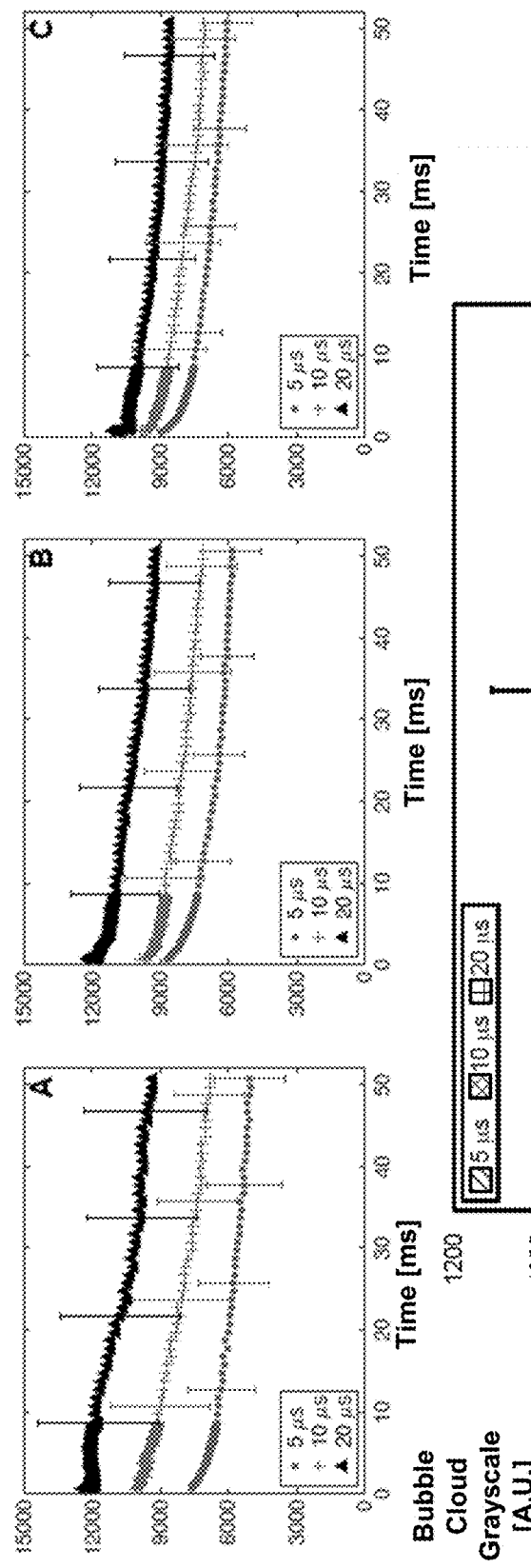
FIG. 14 is a series of diagrams illustrating bubble cloud grayscale values as a function of time for different peak negative pressure histotripsy pulses.

The time-dependent bubble cloud grayscale values for all insonation conditions are shown in FIG. 14. Referring to FIG. 14, bubble cloud grayscale values as a function of time for histotripsy pulses having a (A) 12 MPa, (B) 18 MPa, or (C) 23 MPa peak negative pressure are depicted. The duration of the histotripsy pulse is noted in the legend. Error bars are representative of data throughout the duration of image acquisition. The grayscale values of the bubble cloud remained within 1% over the first millisecond of data collection after application of the histotripsy pulse. Over the 50 ms observation period, bubble cloud grayscale values decreased on average by 30±10.1%. To characterize the decrease in bubble cloud echogenicity, the time-dependent grayscale value (GSV) was fit in the least-squares manner to a function of the form:

$$\frac{GSV}{G_0} = 1 - \alpha t^\beta \quad (9)$$

where $G_0$ is the grayscale value at time t=0. The fitting parameters $\alpha$ and $\beta$, along with the goodness of fit metrics coefficient of determination and root mean squared error are shown in Table 1. Over all insonation conditions, b was found to be 0.54±0.09, and a was 0.04±0.01 236 normalized GSV/s.

Figure 15:
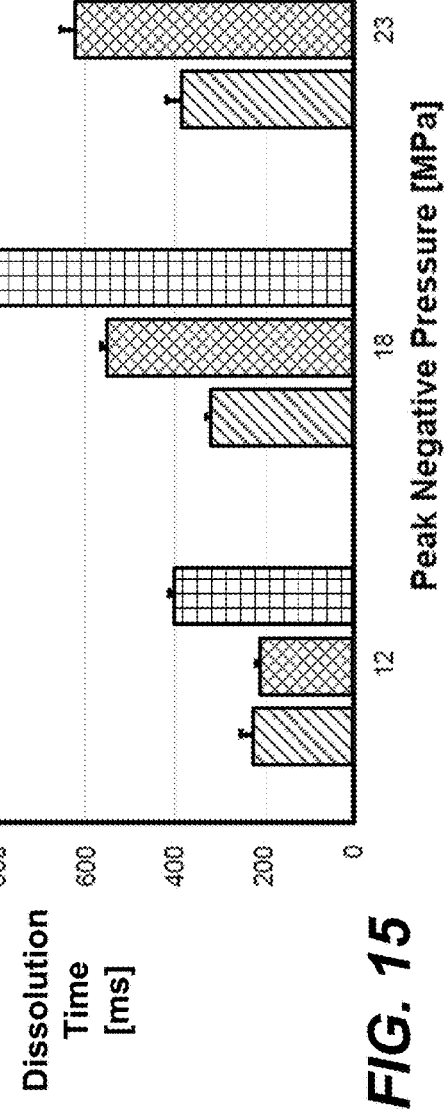
FIG. 15 is a diagram illustrating computed complete bubble cloud dissolution time as a function of the histotripsy insonation parameters.

The time for dissolution of the bubble cloud was computed via the fitting parameters of Eq. (9) as $1/\alpha^{1/\beta}$, and is shown in FIG. 15. At 12 MPa peak negative pressure, the bubble cloud dissolution time was similar for the 5 and 10 μs duration histotripsy pulses, but was increase by a factor of 2 for the 20 μs pulse. For peak negative pressures 18 and 23 MPa, the bubble cloud dissolution time increased with the duration of the histotripsy pulse. The bubble cloud dissolution time increased with the peak negative pressure for the 5 and 10 μs duration histotripsy pulses. For the 20 μs histotripsy pulse, the bubble cloud dissolution time was similar for the peak negative pressures 18 and 23 MPa.

Table 1 illustrates coefficients and parameters for power law fit of the normalized bubble cloud grayscale value (nGSV) as a function of time shown in FIGS. 17A and 17B and used in Equation (9). Goodness-of-fit parameters coefficient of determination ($r^2$) and the root mean square error (RMSE) for the normalized bubble cloud grayscale value (nGSV) are also reported.

Referring to FIG. 15, computed time for complete bubble cloud dissolution via the fitting parameters of Equation (9) as a function of the histotripsy insonation parameters is illustrated. Error bars represent the 95% confidence interval of the least-squares exponential fit to the measured time-dependent bubble cloud grayscale.

TABLE 1

|  | α [nGSV/s$^\beta$] | β [A.U.] | $r^2$ | RMSE [nGSV] |
|---|---|---|---|---|
| 5 μs |  |  |  |  |
| 12 MPa | 0.02 (0.002) | 0.72 (0.02) | 0.996 | 0.005 |
| 18 MPa | 0.05 (0.002) | 0.52 (0.01) | 0.989 | 0.011 |
| 23 MPa | 0.04 (0.003) | 0.54 (0.02) | 0.997 | 0.005 |
| 10 μs |  |  |  |  |
| 12 MPa | 0.04 (0.001) | 0.60 (0.010) | 0.994 | 0.008 |
| 18 MPa | 0.04 (0.001) | 0.51 (0.007) | 0.995 | 0.005 |
| 23 MPa | 0.04 (0.001) | 0.50 (0.024) | 0.994 | 0.006 |
| 20 μs |  |  |  |  |
| 12 MPa | 0.05 (0.001) | 0.50 (0.007) | 0.994 | 0.006 |
| 18 MPa | 0.06 (0.007) | 0.41 (0.025) | 0.989 | 0.007 |
| 23 MPa | 0.03 (0.001) | 0.52 (0.015) | 0.979 | 0.010 |

C. Modulation of Bubble Cloud Grayscale with Imaging Pulse Amplitude

The time-dependent bubble cloud grayscale is shown in FIG. 16 parametrically with the acoustic output from the plane wave imaging pulse (with the peak negative pressure of the plane wave B-mode pulse). Referring to FIG. 16, a normalized bubble cloud grayscale plot (e.g., normalized grayscale values) as a function of time for a (A) 5 μs, (B) 10 μs, or (C) 20 μs duration histotripsy pulse of 23 MPa peak negative pressure is shown. The peak negative pressure of the plane wave imaging pulse is noted in the legend. Error bars are representative of data throughout the duration of image acquisition. The peak negative pressure of the histotripsy pulse was fixed at 23 MPa. The bubble cloud grayscale was decreased more rapidly with increasing output from the imaging array.

Referring to FIGS. 17A and 17B, FIG. 17A is a diagram illustrating complete bubble cloud dissolution time as a function of peak negative pressure of the plane wave imaging pulse, and FIG. 17B is a diagram illustrating a fitting parameter of bubble cloud dissolution calculations as a function of peak negative pressure of the plane wave imaging pulse.

As shown in FIGS. 17A and 17B, time for the bubble cloud dissolution was reduced by 87.4% (255.6 ms), 91.7% (573.2 ms), and 88.3% (749.0 ms) for the 5, 10, and 20 μs pulse durations, respectively. The parameter β did not decrease significantly with increasing output from the imaging array (β=0.46 275±0.06). Because the parameter β is about 0.5, the results indicate a diffusion process occurs at all outputs of the imaging array. However, the term α increased with increasing peak negative pressure of the plane wave B-mode pulse as shown in FIG. 17B. Additionally, the results indicate increased diffusion from the bubble cloud because the term α increases with the output of the imaging array.

The area of the bubble cloud decreased by 4.6±4.9% (12.8±16.6 mm$^2$) for all pressure levels of the imaging array over the 50 ms data acquisition period, similar to that observed for the low output fields in FIG. 13. The azimuthal position of the bubble cloud shifted by approximately 3% (less than 1 mm) over the course of the 50 ms observation period. Overall, these results indicate that while the increased acoustic output from the imaging array decreases the size of individual bubbles within the cloud as indicated by the decrease in grayscale, translation or areal size changes do not occur to the cloud as a whole.

D. Analytic Calculation of Bubble Dynamics

Figure 18:
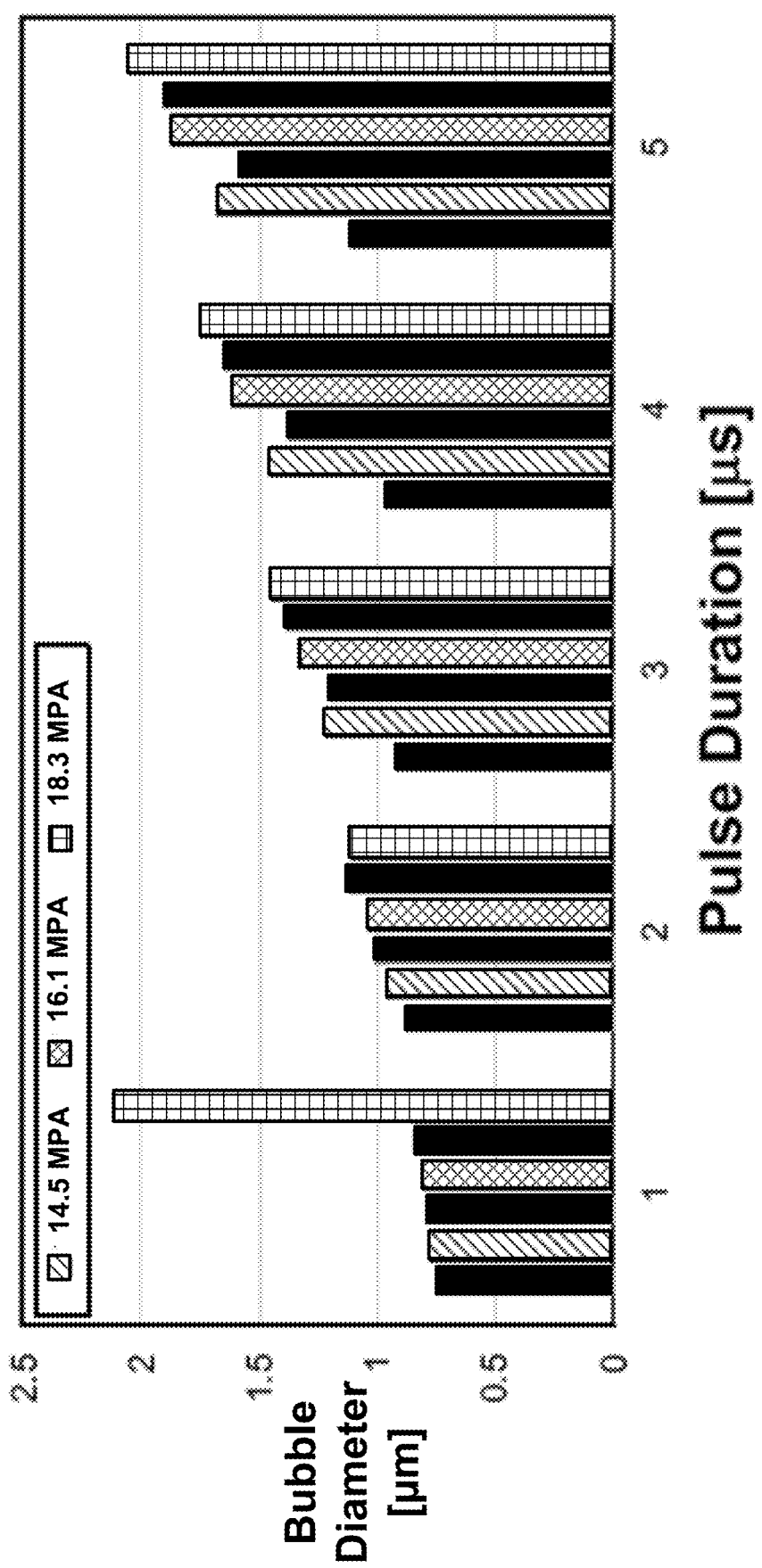
FIG. 18 is a diagram illustrating comparisons of numerical results and analytically predicted values of diffusion-dependent equilibrium bubble diameter as a function of the histotripsy pulse duration.

A comparison of numerical and analytic prediction of the diffusion-dependent equilibrium bubble size as a function of the histotripsy pulse duration is shown in FIG. 18. Referring to FIG. 18, comparisons of numerical results (solid bars) and analytically predicted values (patterned bars) of diffusion-dependent equilibrium bubble diameter as a function of the histotripsy pulse duration are illustrated. The peak negative pressure of the histotripsy pulse is noted in the legend. The initial bubble diameter was 20 nm. As shown in in FIG. 18, for all pulse durations, the predictions of the analytic and numerical models are within 6.8±6.5% (0.10±0.09 μm) for the 16.1 and 18.3 MPa peak negative pressure pulses. The analytic model overpredicts the bubble size by 29.0±21.7% (0.29±0.23 μm) compared to the numerical model for the 14.5 MPa pulse. The validity of the analytic model is proven to predict bubble growth rate accurately for multiple-cycle pulses with peak negative pressures less than 14.7 MPa (Bader and Holland 2016). It has been noted that such methods may overpredict when predicting bubble growth rates at peak negative pressures over 14.7 MPa (Bader and Holland 2016).

Figures 19A, 19B:
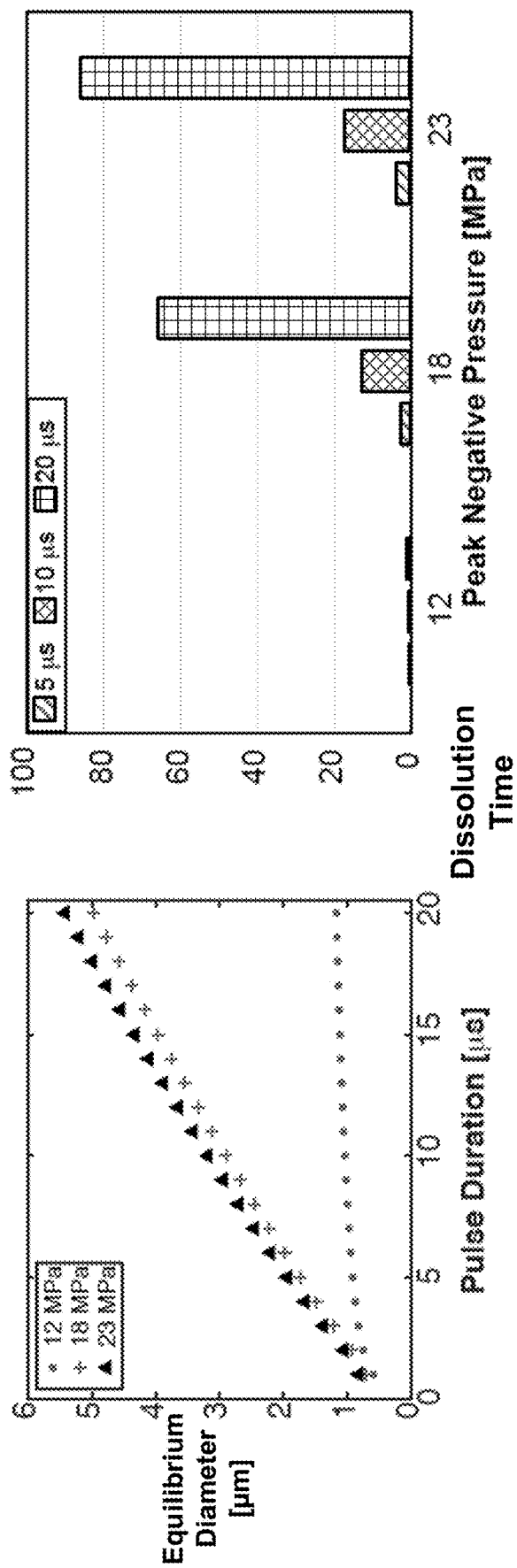
FIG. 19A is a diagram illustrating an analytic prediction of diffusion-dependent equilibrium diameter for insonation conditions.
FIG. 19B is a diagram illustrating an analytic prediction of passive bubble dissolution time based on insonation condition-dependent bubble equilibrium bubble diameter.

The dependence of the diffusion-dependent bubble equilibrium diameter was computed analytically for the insonation conditions considered in this study and is shown in FIG. 19A. Referring to FIG. 19A, analytic prediction of diffusion-dependent equilibrium diameter for insonation conditions considered in this study is illustrated. For the largest two peak negative pressures, the equilibrium bubble diameter increased linearly with the duration of the histotripsy pulse. For the lowest peak negative pressure (12 MPa), the tension was not sufficient to induce strong bubble growth throughout the duration of the pulse (Bader and Holland 2016).

The corresponding predicted time for passive bubble dissolution is shown in FIG. 19B. Referring to FIG. 19B, prediction of passive bubble dissolution time based on insonation condition-dependent bubble equilibrium bubble diameter is illustrated. The bubble dissolution time increases with peak negative pressure for a given pulse duration, and with the pulse duration for a given peak negative pressure. The bubble dissolution time increased with the peak negative pressure of the histotripsy pulse (for fixed pulse durations) or increased with the pulse duration (for fixed peak negative pressures), consistent with experimental observations in FIG. 9A. For the 10- and 20-µs excitations, the predicted bubble dissolution time is longer than 50 ms (65 to 1333 ms), consistent with the trends observed in the changes of bubble cloud grayscale in FIG. 15. In contrast, the predicted dissolution time for bubbles excited by the 5-µs pulses are between 13.2 and 21.6 ms.

III. Discussion

A. Bubble Cloud Dynamics

In this experiment, histotripsy-induced bubble clouds were visualized with high frame rate plane wave imaging. Plane wave imaging can also be utilized in opaque materials with modified the acousto-mechanical properties. Here, studies focused on the change of the bubble cloud after the histotripsy excitation.

One important interesting feature of the bubble clouds observed in this study is the lack of interesting behavior. The bubble cloud position appears stationary within 3% over the observation period, with an approximate 13% reduction in the cloud area. The grayscale of the bubble cloud, indicative of the size of residual bubbles, decreases exponentially over a long time scale, as shown in FIG. 15.

Previous studies have noted the appearance of residual bubble clouds between 30 and 50 ms post excitation (Xu et al. 2007, Prieur et al. 2015, Bader et al. 2018a). The primary bubble cloud collapses within 50-200 µs post excitation. Thus, the bubble clouds captured here are comprised of "residual bubbles" or "daughter bubbles" from the original "mother" cloud. The presence of these slowly changing bubble clouds may be sustained through diffusion of gas from the surrounding media (Bader and Bollen 2018). Diffusion operates over a relatively slow time scale (Neppiras 1980), as compared to coalescence, and consistent with the slow decrease in the bubble cloud grayscale.

The presence of such residual bubble clouds mitigates the treatment efficacy of histotripsy, reactivating bubble activity in discrete locations throughout the focal zone (Wang et al. 2012). This has prompted the development of bubble modulation. For example, applying "bubble deleting pulses" interleaved with therapeutic pulses to minimize the influence of residual bubble clouds (Cain et al. 2015, Shi et al. 2018). Here, a similar effect was observed with the use of high output plane wave ultrasound waves during the high frame rate plane wave image acquisition. Indeed, the decay time and dissolution time decreased.

Using high frame rate imaging instead of a separate source to force bubble dissolution has the advantage of providing feedback of the residual bubble cloud reduction. Indeed, the onset of subsequent pulses could be automated based on grayscale information. Such a scheme would not be possible with a separate bubble deleting source due to constructive interference between the imaging fields and the bubble deleting pulse.

Clinical implementation may dictate that the imaging array be aligned confocally with the therapy source. As the focal distance for most therapy sources is 2-3 times longer (e.g. 60 mm or greater), the 6.25 MHz imaging pulse utilized here will be attenuated significantly (Bader et al. 2016a).

It should be noted that most bubble deleting pulses require pulses less than 3 MPa peak negative pressures to coalesce residual bubbles (Shi et al. 2018), and it might be possible to develop an optimized bubble deleting plane wave sequence.

B. Analytic Predictions of Bubble Diffusion

Results from the analytic model for predicting diffusion during histotripsy-induced bubble expansion were in good agreement with numerical predictions for peak negative pressures 16.1 and 18.3 MPa. There is a divergence of the analytic and numerical predictions as the pulse duration increased, likely due to additive errors in the analytic model. The analytic prediction overestimates diffusion for the 14.5 MPa case because the analytic model over estimates bubble growth beyond the first cycle of the histotripsy pulse (Bader and Holland 2016). Regardless, the analytic and numerical predictions are within 6.8±6.5% (0.10±0.09 µm) for cases where the analytic model is valid. Beyond ease and accessibility compared to numerical calculations, analytic models provide a physical intuition as to the important parameters that effect the bubble dynamics. The identification of such parameters can help guide the development of regulatory standards for emerging therapies like histotripsy.

The trends of equilibrium diameter and bubble dissolution time predicted by the analytic model in FIGS. 19A and 19B are consistent with trends observed in reduction in grayscale. However, the times for bubble dissolution appear much shorter than would be anticipated based on the dissolution times illustrated in FIG. 15. This may be in part due to the nature of the analytic calculation, which models the growth of a single bubble whereas a dense bubble cloud is formed during the shock scattering process (Maxwell et al. 2011b). Thus, any bubble/bubble interactions such as coalescence would not be accounted for in the analytic model. The analytic calculation models the growth of the bubble which scatters the incident shock wave geometrically (Maxwell et al. 2011b). While the initial scattering bubble experiences the tension associated with the incident histotripsy pulse, the tension of the shock scattered from the pressure release boundary condition may be much greater (Maxwell et al. 2010). Larger tensions will lead to larger bubbles (Bader and Holland 2016), and therefore longer diffusion times (Bader and Bollen 2018).

IV. Summary

Overall, the results indicate that high frame rate imaging can be used to both monitor and modulate the behavior of histotripsy bubble clouds during treatment (e.g., interleaved between histotripsy pulses). This is a benefit over previous methods which only monitored the behavior of bubble clouds in between histotripsy sessions or cycles, e.g., after 2000 history pulses stop histotripsy and image.

V. Additional Methods

Additional experiments were conducted on tissue mimicking phantoms subjected to therapeutic ultrasound to determine bubble specific imaging and dissolution. Standard plane wave imaging, pulse inversion imaging, and chirp-coded excitation imaging were utilized to visualize bubble clouds at a 2 kHz frame rate. For all imaging schemes, a monotonic decrease in the bubble cloud grayscale was observed over a 45 ms period following the histotripsy insonation. The change in bubble cloud grayscale was dependent on the imaging scheme, with faster grayscale reduction for larger peak negative pressures of the imaging pulse. Bubble-specific sequences resulted in faster decreases in the bubble cloud grayscale compared with standard plane wave imaging. Overall, these results highlight high-frame rate imaging as a means to monitor and modulate histotripsy bubble cloud dissolution.

A. Introduction

Ultrasound as a therapeutic modality has been under development since the 1950s (O Brien et al. 2015). Histotripsy is a focused ultrasound therapy that imparts lethal mechanical damage to the target tissue via the generation of bubble clouds (Bader et al. 2019), and has the potential to translate for the ablation of numerous pathologies (Khokhlova et al. 2015). Bubble clouds that persisted between histotripsy pulses generate damage at discrete locations within the focal zone, leading to an incomplete tissue disintegration (Wang et al. 2012). Thus, there is a need to ensure the dissolution of bubble clouds between the application of consecutive histotripsy pulses.

Diagnostic ultrasound imaging is the primary modality for monitoring the hyperechoic histotripsy bubble cloud. Conventional B-mode imaging requires tens of milliseconds for image acquisition, over which time the bubble cloud can undergo significant changes and multiple histotripsy pulses may be applied (Maxwell et al. 2011b). Standard plane wave imaging employs all elements in parallel to transmit and receive echoes, shortening the acquisition sequence to less than 100 µs.

The standard plane wave sequence temporal resolution is sufficient to track bubble cloud dissolution (Bader et al. 2019), which provides a potential means to provide feedback for the histotripsy application rate. The imaging pulse interacts with the bubble cloud, resulting in a faster reduction in bubble cloud grayscale with larger peak negative pressures (Bader et al. 2019). Standard plane wave imaging lacks bubble-specific contrast. Such bubble-specific contrast would facilitate bubble cloud detection in an in vivo heterogenous environment. The nonlinear oscillations induced by bubble-specific imaging sequences may also accentuate cloud dissolution (Church 1988).

In this study, histotripsy bubble clouds generated in a tissue mimicking phantom were monitored with high frame rate imaging. Sequences that were bubble inspecific (standard plane wave) and bubble-specific (pulse inversion and chirp-coded excitation) were explored. For each sequence, the contrast-to-noise ratio and time-dependent bubble cloud grayscale were tracked.

B. Methods and Materials i. Experimental Set-Up

A focused source, having a 1 MHz fundamental frequency, a 7.5 cm focal distance, and a 10 cm diameter was driven by a class D amplifier (Hall et al. 2006), (Maxwell et al. 2017) and was used to generate bubble clouds in a tissue mimicking phantom (Bader et al. 2016a). Pulses of a 5 µs duration and a 25 MPa peak negative pressure were applied at a 10 Hz rate. An L11-5v imaging array controlled by a research ultrasound system (Vantage 128, Verasonics, Kirkland, WA, USA) was oriented to monitor bubble cloud activity along the central axis of the therapy source (similar to as shown in FIG. 21). The imaging array acquired images at a 2 kHz frame rate over a 45 ms duration following the histotripsy excitation (similar to as shown in FIG. 20).

ii. Imaging Sequence

The bubble clouds were monitored with either standard plane wave, pulse inversion, or chirp-coded excitation schemes. For the plane wave and pulse inversion acquisitions, the imaging pulse had a 5 MHz fundamental frequency and 0.3 µs pulse duration. For chirp-coded excitation imaging, the pulse bandwidth ranged from 4.8 to 6 MHz over a 2 µs duration. For all sequences, the electrical excitation provided to the imaging array was either 5 V or 25 V. Images were downloaded and processed offline. The threshold grayscale value separating the bubble cloud from background was determined via Otsu's method. For each frame (i.e. timepoint), the bubble cloud area and mean grayscale value was tabulated.

Figures 22, 23:
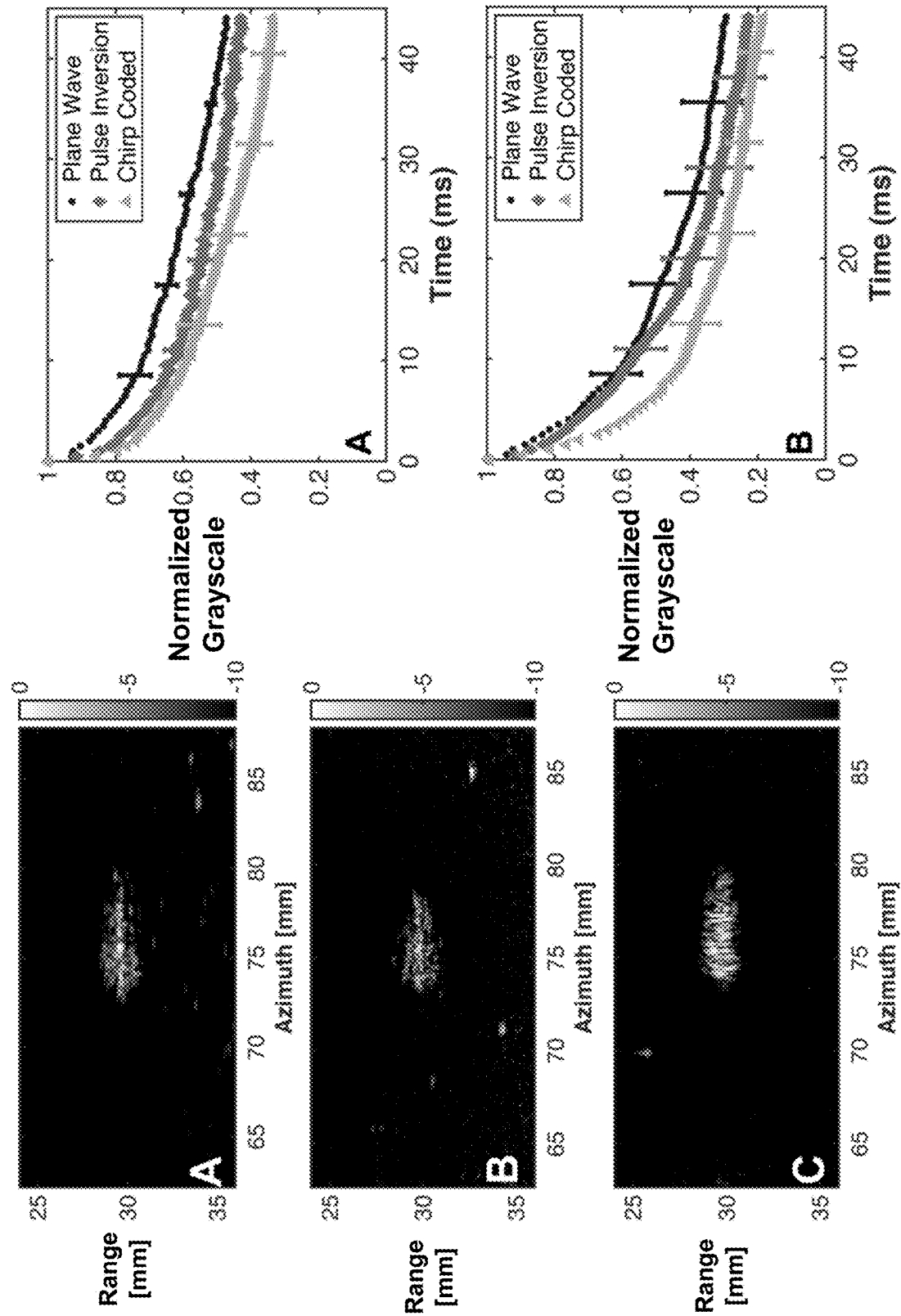
FIG. 22 is a diagram illustrating images of bubble clouds captured by multiple imaging schemes.
FIG. 23 is a diagram illustrating bubble cloud dissolution as a function of time for multiple imaging voltages.

FIG. 22 illustrates bubble clouds visualized in the tissue phantom 10 ms after the histotripsy excitation with (A) Standard plane wave imaging, (B) Pulse inversion imaging, and (C) Chirp-coded excitation sequence imaging. The grayscale colormap is reported in terms of decibels, normalized to the maximum grayscale value. The histotripsy pulse propagates from left to right in the image.

C. Results i. Bubble Cloud Tracking

Bubble clouds generated within the phantom were readily visualized for all tested modalities, as indicated in FIG. 22. For a given voltage applied to the imaging array, no difference was observed in the bubble cloud area between the three imaging schemes (p>0.05 by ANOVA analysis with Tukey HSD post hoc correction). The contrast-to-noise ratio was also not significantly different between the imaging schemes. Both the bubble cloud area and contrast-to-noise ratio were evaluated 10 ms following the histotripsy insonation.

ii. Bubble Cloud Dissolution Profile

The 2 kHz frame rate utilized in this study had sufficient temporal resolution to track bubble cloud dissolution accurately (FIG. 23). FIG. 23 illustrates bubble cloud grayscale as a function of time for (A) 5 V, and (B) 25 V electrical excitations applied to the imaging array. The error bars represent the standard deviation for all acquired data sets for each respective arm (N=3 each arm). The grayscale values are normalized to the peak pixel intensity for the first frame acquired. A slow change in the mean bubble cloud grayscale was observed over the 45 ms observation window with all imaging schemes, with an overall reduction in the bubble cloud grayscale by 50-80%.

Figure 24:
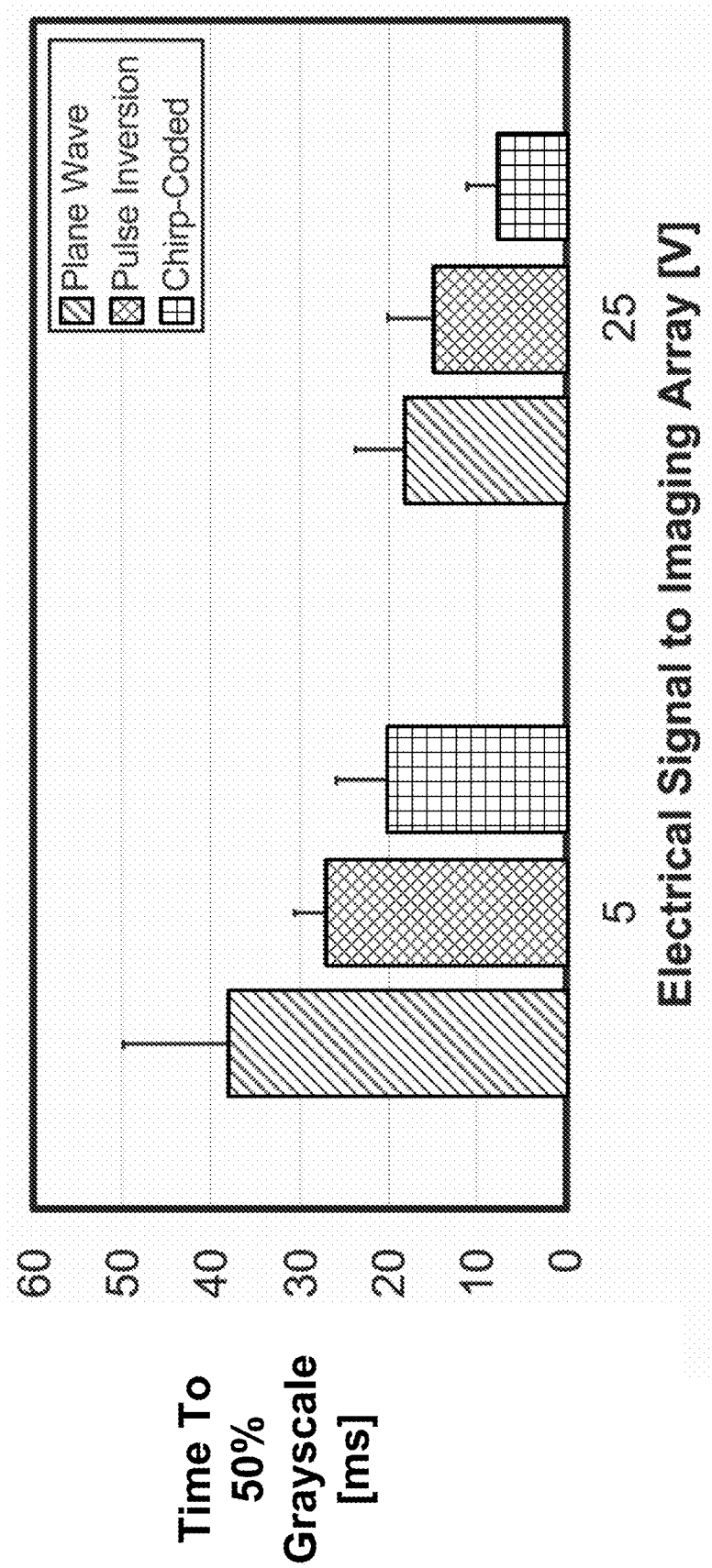
FIG. 24 is a diagram illustrating bubble cloud dissolution time for a 50 percent reduction for multiple imaging schemes.

To characterize the dissolution rate, the time to a 50% reduction in the bubble cloud grayscale was tabulated for all experimental conditions (FIG. 24). FIG. 24 illustrates the time to a 50% reduction in the bubble cloud grayscale for each tested imaging sequence. The error bars represent the standard deviation for each respective arm (N=3 each arm).

A larger electrical signal applied to the imaging array resulted in a significant reduction in the time to 50% bubble cloud grayscale for all the tested imaging sequences (p<0.05). For a given voltage to the imaging array, the time to 50% bubble cloud grayscale was on average shorter for the bubble-specific imaging sequences compared to the standard plane wave imaging sequence. Chirp-coded excitation imaging had the shortest observed time to a 50% reduction in bubble cloud grayscale.

D. Discussion and Conclusions

In this study, histotripsy-generated bubble clouds were visualized following the therapeutic excitation with standard plane wave, pulse inversion, and chirp-coded excitation imaging sequences. Because of the relatively long dissolution time (Bader et al. 2019), the 2 kHz frame rate employed in this study was sufficient to provide accurate tracking of the bubble cloud over the 45 ms observation window. Implementing high-speed feedback based on the bubble cloud grayscale during the application of histotripsy pulses would minimize the so-called cavitation memory effect to ensure uniform ablation of the target tissue (Wang et al. 2012). Such an imaging sequence could complement coalescing bubble sequences (Shi et al. 2018), or be employed on its own to reduce the burden of residual bubble clouds (Bader et al. 2019).

The pulse inversion and chirp-coded excitation sequences form images based on bubble-specific second harmonic emissions, and should provide strong contrast of the bubble cloud compared to standard plane imaging. No differences were noted in the contrast-to-noise ratio for the imaging schemes investigated here. This may be in part due to the low scatter phantom employed in this study (Bader et al. 2016a), which resulted in a uniformly hypoechoic background. Future studies will investigate the ability of each of these schemes to identify bubble clouds in a heterogenous environment in vivo. The nature of histotripsy bubble activity may also have been a contributing factor in the observed similarity of the contrast-to-noise ratio between the imaging schemes. Histotripsy pulses can generate bubbles greater than 100 μm in diameter (Vlaisavljevich et al. 2015). Bubbles of this size may scatter the imaging pulse geometrically (Bader et al. 2012), resulting in a relatively small nonlinear signal.

The bubble cloud dissolution profile was influenced by the imaging parameters, as indicated by the variation in the time to a 50% reduction in bubble cloud grayscale (FIG. 24). The peak negative pressure of the imaging pulse, proportional to the bubble cloud behavior, with chirp-coded excitation schemes resulting in the shortest time to a 50% reduction in the bubble cloud grayscale, and standard plane wave imaging resulting in the longest time. There may be multiple reasons for this observation. The nonlinear bubble oscillations accentuated by bubble-specific sequences and increased peak negative pressure of the imaging pulse will enhance the diffusion of gas into the surrounding medium (Church et al. 1988). The duration of the pulse inversion and chirp-coded excitation schemes are two and ten times longer, respectively, than the standard plane wave sequence. The extended duration of the bubble-specific sequences may generate sustained nonlinear bubble oscillations and therefore a faster cloud dissolution rate (Bader et al. 2012). The population of bubbles producing contrast from the bubble-specific sequences will also vary from the standard plane wave sequences, which may also account for the discrepancy in the observed bubble cloud dissolution profile.

Overall, these results indicate the utility of bubble-specific imaging sequences for monitoring histotripsy bubble cloud dissolution. When implemented as a high frame rate sequence, these imaging methods may provide sufficient feedback for the application of histotripsy pulses for uniform disintegration of the target tissue.

The above specification and examples provide a complete description of the structure and use of illustrative examples. Although certain aspects have been described above with a certain degree of particularity, or with reference to one or more individual examples, those skilled in the art could make numerous alterations to aspects of the present disclosure without departing from the scope of the present disclosure. As such, the various illustrative examples of the methods and systems are not intended to be limited to the particular forms disclosed. Rather, they include all modifications and alternatives falling within the scope of the claims, and implementations other than the ones shown may include some or all of the features of the depicted examples. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one example or may relate to several examples. Accordingly, no single implementation described herein should be construed as limiting and implementations of the disclosure may be suitably combined without departing from the teachings of the disclosure.

The previous description of the disclosed implementations is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims. The claims are not intended to include, and should not be interpreted to include, means-plus- or step-plus-function limitations, unless such a limitation is explicitly recited in a given claim using the phrase(s) "means for" or "step for," respectively.

REFERENCES

[1] Apfel R E 1981 Acoustic Cavitation *Methods in Experimental Physics* vol 19 (New York: Academic Press, Inc) pp 355-411.

[2] Arnal B, Baranger J, Demene C, Tanter M and Pernot M 2017 In vivo real-time cavitation imaging in moving organs *Phys. Med. Biol.* 62 843-57.

[3] Bader K B 2018 The influence of medium elasticity on the prediction of histotripsy-induced bubble expansion and erythrocyte viability *Phys. Med. Biol.* 63 095010-

[4] Bader K B and Bollen V 2018 The influence of gas diffusion on bubble persistence in shock-scattering histotripsy *The Journal of the acoustical Society of America* 143 EL481-6.

[5] Bader K B, Hendley S A, Anthony G J, and Bollen V June 2019 Observation and modulation of the dissolution of histotripsy-induced bubble clouds with high-frame rate plane wave imaging *Phys. Med. Biol.* 64, 115012-115015.

[6] Bader K B and Holland C K 2012 Gauging the likelihood of stable cavitation from ultrasound contrast agents *Phys. Med. Biol.* 58 127-44.

[7] Bader K B and Holland C K 2016 Predicting the growth of nanoscale nuclei by histotripsy pulses *Phys. Med. Biol.* 2947-66.

[8] Bader K B, Crowe M J, Raymond J L and Holland C K 2016a Effect of Frequency-Dependent Attenuation on Predicted Histotripsy Waveforms in Tissue-Mimicking Phantoms *UMB* 42 1701-5.

[9] Bader K B, Haworth K J, Maxwell A D and Holland C K 2018a Post Hoc Analysis of Passive Cavitation Imaging for Classification of Histotripsy-Induced Liquefaction in Vitro *IEEE Trans. Med. Imaging* 37 106-15.

[10] Bader K B, Haworth K J, Shekhar H, Maxwell A D, Peng T, McPherson D and Holland C K 2016b Efficacy of histotripsy combined with rt-PA in vitro *Phys. Med. Biol.* 61 5253-74.

[11] Bader K B, Vlaisavljevich E and Maxwell A D 2018b For whom the bubble grows *UMB* 1-92.

[12] Cain C A, Hall T L, Duryea A P and Roberts W 2015 Removal of residual cavitation nuclei to enhance histotripsy fractionation of soft tissue *IEEE Trans. Ultrason., Ferroelect., Freq. Contr.* 62 2068-78.

[13] Canney M S, Khokhlova V A, Bessonova O V, Bailey M R and Crum L A 2010 Shock-Induced Heating and Millisecond Boiling in Gels and Tissue Due to High Intensity Focused Ultrasound *Ultrasound in Medicine & Biology* 36 250-67.

[14] Church C C 1989 A theoretical study of cavitation generated by an extracorporeal shock wave lithotripter *The Journal of the acoustical Society of America* 86 215.

[15] Church C C 1988 Prediction of rectified diffusion during nonlinear bubble pulsations at biomedical frequencies *J. Acoust. Soc. Am.* 83 2210-7.

[16] Church C C, Labuda C and Nightingale K 2015 A Theoretical Study of Inertial Cavitation from Acoustic Radiation Force Impulse Imaging and Implications for the Mechanical Index *Ultrasound in Medicine & Biology* 41 472-85.

[17] Couture O, Fink M and Tanter M Ultrasound contrast plane wave imaging *IEEE Trans. Ultrason., Ferroelect., Freq. Contr.* 59.

[18] Crum L A and Hansen G M 1982 Generalized equations for rectified diffusion *J. Acoust. Soc. Am.* 72 1586-92.

[19] Duryea A P, Roberts W W, Cain C A and Hall T L 2015 Removal of residual cavitation nuclei to enhance histotripsy erosion of model urinary stones *IEEE Trans. Ultrason., Ferroelect., Freq. Contr.* 62 896-904.

[20] Eller A 1965 Rectified Diffusion during Nonlinear Pulsations of Cavitation Bubbles *The Journal of the acoustical Society of America* 37 493.

[21] Gateau J, Aubry J-F, Pernot M, Fink M and Tanter M 2011 Combined passive detection and ultrafast active imaging of cavitation events induced by short pulses of high-intensity ultrasound *IEEE Trans. Ultrason., Ferroelect., Freq. Contr.* 58 517-32.

[22] Hall T and Cain C 2006 A low cost compact 512 channel therapeutic ultrasound system for transcutaneous ultrasound surgery 829 445.

[23] Hall T, Fowlkes J and Cain C 2007 A real-time measure of cavitation induced tissue disruption by ultrasound imaging backscatter reduction *IEEE Trans. Ultrason., Ferroelect., Freq. Contr.* 54 569-75.

[24] Haworth K J, Salgaonkar V A, Corregan N M, Holland C K and Mast T D 2015 Using passive cavitation images to classify high-intensity focused ultrasound lesions *Ultrasound in Medicine & Biology* 41 2420-34.

[25] Holland C K and Apfel R E 1989 Improved Theory for the Prediction of Microcavitation Thresholds *IEEE transactions on ultrasonics, ferroelectrics, and frequency control* 36 204-8.

[26] Hu H, Xu S, Yuan Y, Liu R, Wang S and Wan M 2015 Spatial-temporal ultrasound imaging of residual cavitation bubbles around a fluid-tissue interface in histotripsy *The Journal of the acoustical Society of America* 137 2563-72.

[27] Khokhlova T D, Canney M S, Khokhlova V A, Sapozhnikov O A, Crum L A and Bailey M R 2011 Controlled tissue emulsification produced by high intensity focused ultrasound shock waves and millisecond boiling *The Journal of the acoustical Society of America* 130 3498.

[28] Khokhlova V A, Fowlkes J B, Roberts W W, Schade G R, Xu Z, Khokhlova T D, Hall T L, Maxwell A D, Wang Y-N and Cain C A 2015 Histotripsy methods in mechanical disintegration of tissue: Towards clinical applications *Int J Hyperthermia* 31 145-62.

[29] Landau L D and Lifshitz E M 1987 *Fluid Mechanics* vol 6 (Elmsford).

[30] Lastman G J and Wentzell R A 1981 Comparison of five models of spherical bubble response in an inviscid compressible liquid *Journal of the Acoustical Society of America* 69 638-42.

[31] Maxwell A D, Cain C A, Fowlkes J B and Xu Z 2010 Inception of cavitation clouds by scattered shockwaves 108-11.

[32] Maxwell A D, Cain C A, Hall T L, Fowlkes J B and Xu Z 2013 Probability of Cavitation for Single Ultrasound Pulses Applied to Tissues and Tissue-Mimicking Materials *Ultrasound in Medicine & Biology* 39 449-65.

[33] Maxwell A D, Owens G, Gurm H S, Ives K, Myers D D Jr and Xu Z 2011 Noninvasive Treatment of Deep Venous Thrombosis Using Pulsed Ultrasound Cavitation Therapy (Histotripsy) in a Porcine Model *Journal of Vascular and Interventional Radiology* 22 369-77.

[34] Maxwell A D, Wang T-Y, Cain C A, Fowlkes J B, Sapozhnikov O A, Bailey M R and Xu Z 2011b Cavitation clouds created by shock scattering from bubbles during histotripsy *The Journal of the acoustical Society of America* 130 1888.

[35] Maxwell A, Sapozhnikov O, Bailey M, Crum L, Xu Z, Fowlkes B, Cain C and Khokhlova V 2012 Disintegration of tissue using high intensity focused ultrasound: two approaches that utilize shock waves *Acoustics Today* 8 24-37.

[36] Maxwell A D, Yuldashev P, Kreider W, Khokhlova D, Schade G R, Hall T L, Sapozhnikov O A, Bailey M R, and Khokhlova V A August 2017 A Prototype Therapy System for Transcutaneous Application of Boiling Histotripsy *IEEE Trans. Ultrason., Ferroelect., Freq. Contr.* 64 1547-1557.

[37] Muhr A H and Blanshard J M V 1982 Diffusion in gels *Polymer* 23 1012-26.

[38] Neppiras E A 1980 Acoustic cavitation *Physics reports* 61 159-251.

[39] O Brien and Dunn October 2015 An early history of high-intensity focused ultrasound *Phys. Today* 68 40-45.

[40] Prieur F, Zorgani A, Catheline S, Souchon R, Mestas J-L, Lafond M and Lafon C 2015 Observation of a cavitation cloud in tissue using correlation between ultrafast ultrasound images *IEEE Trans. Ultrason., Ferroelect., Freq. Contr.* 62 1256-64.

[41] Radhakrishnan K, Bader K B, Haworth K J, Kopechek J A, Raymond J L, Huang S-L, McPherson D D and Holland C K 2013 Relationship between cavitation and loss of echogenicity from ultrasound contrast agents *Phys. Med. Biol.* 58 6541-63.

[42] Raymond J L, Luan Y, Peng T, Huang S-L, McPherson D D, Versluis M, de Jong N and Holland C K 2016 Loss of gas from echogenic liposomes exposed to pulsed ultrasound *Phys. Med. Biol.* 61 8321

[43] Rosnitskiy P B, Yuldashev P V, Sapozhnikov O A, Maxwell A D, Kreider W, Bailey M R and Khokhlova V A 2017 Design of HIFU Transducers for Generating Specified Nonlinear Ultrasound Fields *IEEE Trans. Ultrason., Ferroelect., Freq. Contr.* 64 374-90.

[44] Schuster T G, Wei J T, Hendlin K, Jahnke R and Roberts W W 2018 Histotripsy Treatment of Benign Prostatic Enlargement Using the Vortx R x System: Initial Human Safety and Efficacy Outcomes *Urology* 114 184-7.

[45] Shi A, Lundt J, Deng Z, Macoskey J, Gurm H, Owens G, Zhang X, Hall T L and Xu Z 2018 Integrated Histotripsy and Bubble Coalescence Transducer for Thrombolysis *Ultrasound Med. Biol.* 44 2697-2709.

[46] Shi A, Xu Z, Lundt J, Tamaddoni H A, Worlikar T and Hall T L 2018b Integrated Histotripsy and Bubble Coalescence Transducer for Rapid Tissue Ablation *IEEE Trans. Ultrason., Ferroelect., Freq. Contr.* 65 1822-31.

[47] Szabo T L 2004 *Diagnostic Ultrasound Imaging: Inside Out (Biomedical Engineering)* (Academic Press).

[48] Vlaisavljevich E, Kim Y, Allen S, Owens G, Pelletier S, Cain C, Ives K and Xu Z 2013a Image-Guided Non-Invasive Ultrasound Liver Ablation Using Histotripsy: Feasibility Study in an In Vivo Porcine Model *UMB* 39 1398-409.

[49] Vlaisavljevich E, Kim Y, Allen S, Owens G, Pelletier S, Cain C, Ives K and Xu Z 2013b Image-guided non-invasive ultrasound liver ablation using histotripsy *Ultrasound in Medicine & Biology* 39 1398-409.

[50] Vlaisavljevich E, Lin K-W, Warnez M T, Singh R, Mancia L, Putnam A J, Johnsen E, Cain C and Xu Z 2015 Effects of tissue stiffness, ultrasound frequency, and pressure on histotripsy-induced cavitation bubble behavior *Phys. Med. Biol.* 2271-92.

[51] Wang T-Y, Xu Z, Hall T L, Fowlkes J B and Cain C A 2012 An Efficient Treatment Strategy for Histotripsy by Removing Cavitation Memory *Ultrasound in Medicine & Biology* 38 753-66 Online: http://dx.doi.org/10.1016/j.ultrasmedbio.2012.01.013.

[52] Xu Z, Hall T L, Fowlkes J B and Cain C A 2007 Optical and acoustic monitoring of bubble cloud dynamics at a tissue-fluid interface in ultrasound tissue erosion *The Journal of the acoustical Society of America* 121 2421.

The invention claimed is:

1. A therapeutic ultrasound system comprising:
a transducer configured to emit therapy ultrasound waves towards a therapy site;
an ultrasound imaging device configured to emit pulse inversion plane wave ultrasound waves or chirp-coded excitation plane wave ultrasound waves towards the therapy site and having a focus area of 2-4 centimeters, wherein the ultrasound imaging device is configured to operate in a B-mode and a plurality of image elements emit at a first time and detect at a second time; and
a controller coupled to the transducer and the ultrasound imaging device, the controller configured to:
send an activation signal to the transducer to cause application of the therapy ultrasound waves towards the therapy site;
send an activation signal to the ultrasound imaging device to cause the pulse inversion plane wave ultrasound waves or the chirp-coded excitation plane wave ultrasound waves to begin to be applied i) simultaneously with a last pulse of the therapy ultrasound waves, or ii) at least 5 microseconds (µs) after a start of the last pulse of the therapy ultrasound waves and less than 179 us after the start of the last pulse of the therapy ultrasound waves;
receive image data from the ultrasound imaging device; and
generate bubble cloud image data based on the received image data.

2. The therapeutic ultrasound system of claim 1, wherein the therapy ultrasound waves are configured to generate bubbles at the therapy site and, wherein the pulse inversion plane wave ultrasound waves or the chirp-coded excitation plane wave ultrasound waves are configured to cause the bubbles to diffuse into tissue of the therapy site.

3. The therapeutic ultrasound system of claim 1, wherein the controller is further configured to calculate bubble deletion during a treatment session based on the bubble cloud image data, wherein the controller is further configured to adjust one or more parameters of the transducer, the ultrasound imaging device, or both, based on the calculated bubble deletion, and wherein the treatment session includes multiple cycles of the therapy ultrasound waves and the pulse inversion plane wave ultrasound waves or the chirp-coded excitation plane wave ultrasound waves interleaved together.

4. The therapeutic ultrasound system of claim 1, wherein the transducer is arranged orthogonal to the ultrasound imaging device such that a focus direction of the transducer is orthogonal to a focus direction of the ultrasound imaging device, and wherein the ultrasound imaging device is aligned confocally with the transducer.

5. The therapeutic ultrasound system of claim 1, wherein the ultrasound imaging device comprises a plane wave B-mode device, and wherein the ultrasound imaging device is further configured to:
receive a backscatter signal generated based on the pulse inversion plane wave ultrasound waves or the chirp-coded excitation plane wave ultrasound waves; and
generate the image data based on the backscatter signal.

6. The therapeutic ultrasound system of claim 1, wherein the therapy ultrasound waves comprise pulses and have a pulse length of 3-40 µs, wherein an exposure time of pulses of the therapy ultrasound waves is 5-60 ms, or both.

7. The therapeutic ultrasound system of claim 6, wherein a fundamental frequency of the therapy ultrasound waves is 800 kHz to 1200 kHz, wherein a pulse repetition frequency of the pulses of the therapy ultrasound waves is 10-30 Hertz, or both.

8. The therapeutic ultrasound system of claim 1, wherein a peak negative pressure of the therapy ultrasound waves is 10-20 MPa, a derated focal peak negative pressure of the therapy ultrasound waves is 10-30 MPa, a derated peak positive pressure of the therapy ultrasound waves is 50-150 MPa, a peak negative pressure of the pulse inversion plane wave ultrasound waves or the chirp-coded excitation plane wave ultrasound waves is 300 kPA to 10 MPa, or a combination thereof.

9. The therapeutic ultrasound system of claim 1, wherein the activation signal is configured to cause the ultrasound imaging device to emit the pulse inversion plane wave ultrasound waves, wherein a fundamental frequency of the pulse inversion plane wave ultrasound waves is about 5

MHz, and wherein a pulse duration of the pulse inversion plane wave ultrasound waves is 0.3 μs.

10. The therapeutic ultrasound system of claim 1, wherein a frame rate of the ultrasound imaging device is about 2 kHz, wherein the pulse inversion plane wave ultrasound waves or the chirp-coded excitation plane wave ultrasound waves are applied 147 μs to 179 μs after the start of the last pulse of the therapy ultrasound waves, and wherein a treatment session includes multiple therapy cycles and the last pulse is a last pulse of a particular therapy cycle of the multiple therapy cycles.

11. The therapeutic ultrasound system of claim 1, wherein the activation signal is configured to cause the ultrasound imaging device to emit the chirp-coded plane wave ultrasound excitation waves, wherein a pulse bandwidth of the chirp-coded excitation plane wave ultrasound waves is between 4.8 to 6 MHz, and wherein an application duration of the chirp-coded plane wave ultrasound excitation waves is 2 μs.

12. A method performed by the therapeutic ultrasound system of claim 1, the method comprising:
applying therapy ultrasound waves towards a therapy site;
applying pulse inversion plane wave ultrasound waves or chirp-coded excitation plane wave ultrasound waves towards the therapy site and with a focus area of 2-4 centimeters, wherein the pulse inversion plane wave ultrasound waves or the chirp-coded excitation plane wave ultrasound waves are applied i) simultaneously with a last pulse of the therapy ultrasound waves, or ii) at least 5 microseconds (μs) after a start of the last pulse of the therapy ultrasound waves and less than 179 μs after the start of the last pulse of the therapy ultrasound waves;
receiving, a backscatter signal from the therapy site based on the pulse inversion plane wave ultrasound waves or the chirp-coded excitation plane wave ultrasound waves;
generating image data based on the backscatter signal; and
outputting the image data based on the backscatter signal.

13. The method of claim 12, further comprising:
applying second pulse inversion plane wave ultrasound waves or second chirp-coded excitation plane wave ultrasound waves towards the therapy site, wherein the pulse inversion plane wave ultrasound waves or the chirp-coded excitation plane wave ultrasound waves have a higher frequency than the second pulse inversion plane wave ultrasound waves or the second chirp-coded excitation plane wave ultrasound waves, and wherein the second pulse inversion plane wave ultrasound waves or the second chirp-coded excitation plane wave ultrasound waves are applied after the pulse inversion plane wave ultrasound waves or the chirp-coded excitation plane wave ultrasound waves;
generating second image data based on a second backscatter signal based on the second pulse inversion plane wave ultrasound waves or the second chirp-coded excitation plane wave ultrasound waves; and
calculating bubble deletion parameters based on the image data and the second image data.

14. The method of claim 13, wherein i) the pulse inversion plane wave ultrasound waves or the chirp-coded excitation plane wave ultrasound waves are applied 10 μs to 179 μs after the therapy ultrasound waves; ii) the second pulse inversion plane wave ultrasound waves or the second chirp-coded excitation plane wave ultrasound waves are applied 10 ms after the therapy ultrasound waves; iii) multiple backscatter signals are received over a 10-50 ms imaging period based on a plurality of pulses of the pulse inversion plane wave ultrasound waves or the chirp-coded excitation plane wave ultrasound waves and a plurality of pulses of the second pulse inversion plane wave ultrasound waves or the second chirp-coded excitation plane wave ultrasound waves; iv) the method further comprises generating multiple frames of image data based on the multiple backscatter signals; or a combination thereof.

15. The method of claim 12, further comprising:
brightness mode converting the image data to generate a grayscale bubble cloud image; and
binarize converting the grayscale bubble cloud image to generate a binarized bubble cloud image.

16. The therapeutic ultrasound system of claim 1, wherein the ultrasound imaging device is further configured to emit second plane wave ultrasound waves towards the therapy site, the second plane wave ultrasound waves having a second frequency different from a first frequency of the pulse inversion plane wave ultrasound waves or the chirp-coded excitation plane wave ultrasound waves, wherein the controller is further configured to send an activation signal to the ultrasound imaging device to cause the second plane wave ultrasound waves to be applied 10 milliseconds after the start of the last pulse of the therapy ultrasound waves.

17. The therapeutic ultrasound system of claim 1, wherein the therapy ultrasound waves comprise pulses and have a pulse length of 3-9 μs, wherein a fundamental frequency of the therapy ultrasound waves is 800 kHz to 1100 kHz, wherein a pulse repetition frequency of the pulses of the therapy ultrasound waves is 10-30 Hertz, or a combination thereof.

18. The therapeutic ultrasound system of claim 1, wherein the controller is further configured to:
send an activation signal to the transducer to cause application of second therapy ultrasound waves towards the therapy site, wherein the therapy ultrasound waves are part of a first cycle of a treatment session and the second therapy ultrasound waves are part of a second cycle of the treatment session;
send a second activation signal to the ultrasound imaging device to cause second pulse inversion plane wave ultrasound waves or second chirp-coded excitation plane wave ultrasound waves to begin to be applied i) simultaneously with a last pulse of the second therapy ultrasound waves, or ii) at least 5 microseconds (μs) after a start of the last pulse of the second therapy ultrasound waves and less than 179 microseconds (μs) after i) simultaneously with a last pulse of the second therapy ultrasound waves, or ii) at least 5 microseconds (μs) after a start of the last pulse of the second therapy ultrasound waves and a start of a last pulse of the second therapy ultrasound waves;
receive second image data from the ultrasound imaging device corresponding to the second pulse inversion plane wave ultrasound waves or the second chirp-coded excitation plane wave ultrasound waves;
generate second bubble cloud image data based on the received second image data;
calculate bubble deletion based on the bubble cloud image data and the second bubble cloud image data; and
adjust one or more parameters of the transducer, the ultrasound imaging device, or both, based on the calculated bubble deletion.

19. The therapeutic ultrasound system of claim 1, wherein the activation signal sent to the ultrasound imaging device causes the pulse inversion plane wave ultrasound waves or the chirp-coded excitation plane wave ultrasound waves to begin to be applied simultaneously with the last pulse of the therapy ultrasound waves.

20. The therapeutic ultrasound system of claim 1, wherein the activation signal sent to ultrasound imaging device causes the pulse inversion plane wave ultrasound waves or the chirp-coded excitation plane wave ultrasound waves to begin to be applied at least 5 μs after the start of the last pulse of the therapy ultrasound waves and less than 179 μs after the start of the last pulse of the therapy ultrasound waves.

* * * * *

UNITED STATES PATENT AND TRADEMARK OFFICE
CERTIFICATE OF CORRECTION

| | | |
|---|---|---|
| PATENT NO. | : 12,179,041 B2 | Page 1 of 1 |
| APPLICATION NO. | : 16/809732 | |
| DATED | : December 31, 2024 | |
| INVENTOR(S) | : Kenneth B. Bader and Viktor Bollen | |

It is certified that error appears in the above-identified patent and that said Letters Patent is hereby corrected as shown below:

In the Claims

In Claim 1, Column 40, Line 8, delete "us" and insert --µs-- therefor.

In Claim 18, Column 42, Line 49, delete "i) simultaneously with a last pulse of the second therapy ultrasound waves, or ii) at least 5 microseconds (µs) after a start of the last pulse of the second therapy ultrasound waves and".

Signed and Sealed this
Fourth Day of March, 2025

Coke Morgan Stewart
*Acting Director of the United States Patent and Trademark Office*